United States Patent [19]

Karjalainen et al.

[11] 4,443,466
[45] Apr. 17, 1984

[54] 4-BENZYL- AND 4-BENZOYL-SUBSTITUTED IMIDAZOLE DERIVATIVES AND USE AS MEDICAMENTS

[75] Inventors: Arto J. Karjalainen; Kauko O. A. Kurkela, both of Oulu, Finland

[73] Assignee: Farmos-Yhtyma OY (Farmos Group Ltd.), Turku, Finland

[21] Appl. No.: 242,234

[22] Filed: Mar. 10, 1981

Related U.S. Application Data

[63] Continuation-in-part of Ser. No. 64,575, Aug. 7, 1979, abandoned.

[30] Foreign Application Priority Data

| Jan. 8, 1980 | [EP] | European Pat. Off. ....... 80 302 637.6 |
| Jan. 8, 1980 | [FI] | Finland ................................ 802404 |
| Jan. 8, 1980 | [IL] | Israel ....................................... 60723 |
| Jan. 8, 1980 | [NZ] | New Zealand ........................ 194536 |
| May 8, 1980 | [AU] | Australia ............................. 61071/80 |
| May 8, 1980 | [IE] | Ireland ................................. 1626/80 |
| Jun. 8, 1980 | [CA] | Canada .................................. 357663 |
| Jun. 8, 1980 | [DK] | Denmark ............................ 3385/80 |
| Jun. 8, 1980 | [DD] | German Democratic Rep. ... 223182 |
| Jun. 8, 1980 | [HU] | Hungary ............................. 1955/80 |
| Jun. 8, 1980 | [JP] | Japan ............................... 55-108786 |
| Jun. 8, 1980 | [NO] | Norway ................................ 802352 |
| Jun. 8, 1980 | [ZA] | South Africa ...................... 80/4787 |
| Jun. 8, 1980 | [SU] | U.S.S.R. .............................. 2959548 |

[51] Int. Cl.³ ................. C07D 233/66; C07D 233/54; A61K 31/40

[52] U.S. Cl. .................................. 424/274; 548/343; 548/342; 548/235

[58] Field of Search ....................... 548/343, 342, 235; 424/273 R

[56] References Cited

U.S. PATENT DOCUMENTS 2,895,959  7/1959  Jeffreys et al. ...................... 548/235

OTHER PUBLICATIONS

Novak; J. J. K., Chem. Abs., 84:30780t (1976).
Somin; I. N., Chem. Abs., 71:124547u (1969).

Primary Examiner—Henry R. Jiles
Assistant Examiner—Robert C. Whittenbaugh
Attorney, Agent, or Firm—Burns, Doane, Swecker & Mathis

[57] ABSTRACT

The invention provides compounds of the formula:

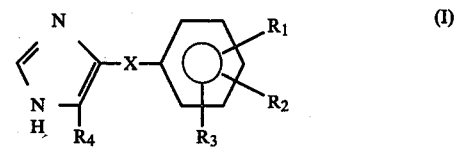

wherein $R_1$, $R_2$ and $R_3$, which can be the same or different, are each hydrogen, chloro, bromo, fluoro, methyl, ethyl, methoxy, amino, hydroxy or nitro; $R_4$ is hydrogen or alkyl of 1 to 7 carbon atoms; —X— is

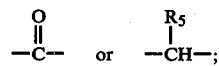

$R_5$ is hydrogen, hydroxy or —$OR_6$; and $R_6$ is alkyl of 1 to 7 carbon atoms or aryl of 6 to 10 carbon atoms; and their non-toxic pharmaceutically acceptable acid addition salts and mixtures thereof. Processes for the preparation and use of the subject compounds are described, as are novel pharmaceutical compositions comprising at least one of the subject compounds or their salts. The compounds and their non-toxic salts exhibit valuable pharmacological activity and are useful in the treatment of mammals, e.g., as anti-ulcer or anti-hypertensive agents. Furthermore, they are useful as diuretic, sedative, analgesic, anti-inflammatory and tranquilizing agents.

141 Claims, No Drawings

4-BENZYL- AND 4-BENZOYL-SUBSTITUTED IMIDAZOLE DERIVATIVES AND USE AS MEDICAMENTS

CROSS-REFERENCE TO RELATED APPLICATION

This is a continuation-in-part of our earlier copending application Ser. No. 64,575, filed Aug. 7, 1979, now abandoned, assigned to the assignee hereof, and hereby incorporated by reference in its entirety and relied upon.

TECHNICAL FIELD OF THE INVENTION

The present invention relates to certain novel 4-benzylimidazole and 4-benzoylimidazole derivatives and their non-toxic, pharmaceutically acceptable acid addition salts, and to pharmaceutical compositions thereof. The invention further relates to processes for preparing the derivatives and to methods employing the derivatives and their salts as anti-hypertensive, anti-ulcer, diuretic, sedative, analgesic, anti-inflammatory and tranquilizing agents in mammals.

SUMMARY OF THE PRIOR ART

A wide variety of compounds possessing anti-hypertensive properties are known in the art. According to their pharmacological mechanism, these compounds can be grouped as follows:

1. Diuretics, e.g., tienilic acid (U.S. Pat. No. 3,758,606), metolazone (U.S. Pat. No. 3,360,518) and bumetanide (U.S. Pat. No. 3,634,583);
2. Stimulants of central α-adrenergic receptors, e.g., clonidine (U.S. Pat. No. 3,202,660), imidazole derivatives [Jen et al, *J. Med. Chem.* 18 (1975), 90], guanabenz (German OLS No. 1,802,364), BS 100-141 (French Pat. No. 1,584,670), tiamenidine (German OLS No. 1,941,761), guanazodine (British Pat. No. 1,216,096) and guanethidine (U.S. Pat. No. 2,928,829);
3. α-Adrenergic blocking agents, e.g., prazosin (U.S. Pat. No. 3,511,836);
4. β-Adrenergic blocking agents, e.g., propranolol (U.S. Pat. No. 3,337,628) and metoprolol (German Pat. No. 2,106,209);
5. Dopamine- β-hydroxylase inhibitors, e.g., bupicomide (U.S. Pat. No. 3,519,717 and German OLS No. 2,217,084);
6. Norepinephrine-depleting drugs, e.g., MJ 10459-2 [Mathier et al, *J. Med. Chem.* 16 (1973) 901];
7. Inhibitors of the renin-angiotensin system, e.g., saralasine (U.S. Pat. No. 3,751,404 and German Pat. No. 2,127,393); and
8. Peripheral vasodilators, e.g., minoxidil (U.S. Pat. No. 3,644,364).

Many anti-ulcer agents are also known in the art, for example, the H₂-antihistamine cimetidine (U.S. Pat. No. 3,876,647), timoprazole (U.S. Pat. No. 4,045,563 and CP-26154 (U.S. Pat. No. 3,922,345), carbenoxolone sodium, certain anticholinergic compounds and postaglandin derivatives [Langman, *Drugs* 14 (1977), 105-115].

Some benzylimidazole and benzoiylimidazole derivatives and related compounds have been previously described, i.e.:

4(5)-benzylimidazole (C.A. 86:106471v, C.A. 84:104657v, C.A. 84:135543j);
4(5)-benzyl-5(4)-methylimidazole (C.A. 78:P97652k, C.A. 58:13935f and C.A. 54:15360h);
5(4)-methyl-4(5)-(2',5'-dimethylbenzyl)imidazole (C.A. 58:13935g);
5(4)-methyl-4(5)-(α-phenyl)methoxymethylimidazole (C.A. 88:164250z, and C.A. 87:152077q);
4(5)benzolylimidazole (C.A. 86:106471v); and
5(4)-ethyl-4(5)-benzylimidazole [*Chem. Ber.* 93, 723-36 (1960); C.A. 78:P97652k].

However, for the most part the prior art does not disclose any pharmaceutical utility whatsoever for the above-mentioned imidazoles. Moreover, although various pharmacological, particularly anti-hypertensive, activities have been previously ascribed to certain 4(5)-benzylimidazoles in French Demande No. 71.37641 (Publication No. 2,122,395), in fact, 4(5)-benzyl-5(4)-methylimidazole and 5(4)-ethyl-4(5)-benzylimidazole, which are described in that French patent publication, have been found by our experiments to have no antihypertensive activity. For example, 4-benzyl-5-methylimidazole in our tests has no blood pressure lowering effect in rats at any dosage; on the contrary, the blood pressure rises with a dosage of 1 mg/kg i.v. in rats.

OBJECT AND SUMMARY OF THE INVENTION

It is an object of the present invention to provide a class of non-toxic imidazole derivatives and their non-toxic acid addition salts which are useful as pharmaceuticals, particularly as anti-ulcer, anti-hypertensive, diuretic, sedative, analgesic, anti-inflammatory and tranquilizing agents.

It is another object of the present invention to provide processes for preparing the non-toxic imidazole derivatives.

It is a further object of the present invention to provide a method for treating mammals with the non-toxic imidazole derivatives and their non-toxic acid addition salts.

Yet a further object of the present invention is to provide novel pharmaceutical compositions of matter comprising at least one of the subject compounds or a non-toxic salt thereof and a pharmaceutically acceptable carrier therefor.

In accordance with the foregoing, the present invention provides compounds of the formula

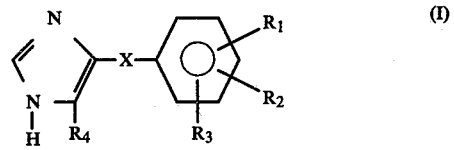

(I)

wherein $R_1$, $R_2$ and $R_3$, which can be the same or different, are each hydrogen, chloro, bromo, fluoro, methyl, ethyl, methoxy, amino hydroxy or nitro; $R_4$ is hydrogen or alkyl of 1 to 7 carbon atoms; —X— is

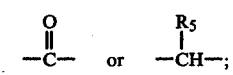

$R_5$ is hydrogen, hydroxy or —$OR_6$; and $R_6$ is alkyl of 1 to 7 carbon atoms or aryl of 6 to 10 carbon atom (e.g, phenyl); and their non-toxic pharmaceutically acceptable acid addition salts and mixtures thereof.

The compounds of formula (I) are preferably defined in that (a) when $R_1$, $R_2$ and $R_3$ are simultaneously hydrogen and $R_4$ is hydrogen or methyl, then —X— is other than

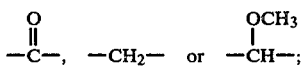

(b) when $R_1$, $R_2$, $R_3$ are simultaneously hydrogen and $R_4$ is ethyl, then —X— is other than —$CH_2$—; and (c) when $R_1$ is 2-methyl, $R_2$ is 5-methyl, $R_3$ is hydrogen and $R_4$ is methyl, then —X— is other than —$CH_2$—. The compounds of formula (I) are more preferably those in which $R_1$, $R_2$, $R_3$ and $R_4$ are defined as above provided that: (a) when $R_1$, $R_2$ and $R_3$ are simultaneously hydrogen, then —X— is other than

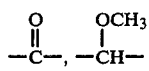

or —$CH_2$—; and (b) when $R_1$ is 2-methyl, $R_2$ is 5-methyl, $R_3$ is hydrogen and $R_4$ is methyl, then —X— is other than —$CH_2$—.

In another aspect, the present invention provides advantageous processes for the preparation of compounds of formula (I) above.

In yet another aspect, the invention provides novel pharmaceutical compositions of matter comprising at least one of the compounds of formula (I) or a non-toxic, pharmaceutically acceptable salt thereof, and a pharmaceutically acceptable carrier therefor.

In a still further aspect, the present invention provides a method for treating a mammal in need of an anti-hypertensive, anti-ulcer, diuretic, sedative, analgesic, anti-inflammatory or tranquilizing agent, which method comprises administering to said mammal an effective amount of at least one compound selected from the group consisting of compounds of formula (I) and the non-toxic, pharmaceutically acceptable acid addition salts thereof. Alternately, said method comprises the administration of a composition comprising an effective amount of at least one compound selected from the group consisting of compounds of formula (I) and the non-toxic, pharmaceutically acceptable acid addition salts thereof, and a pharmaceutically acceptable carrier therefrom.

Other objects, aspects and advantages of the present invention will become apparent from the description which follows:

DETAILED DESCRIPTION OF THE INVENTION AND THE PREFERRED EMBODIMENTS

As stated above, the present invention relates to certain non-toxic imidazole derivatives of formula (I) and their non-toxic, pharmaceutically active acid addition salts. The imidazole derivatives are specifically 4-benzyl- and 4-benzoylimidazole derivatives of the following formulas (Ia) and (Ib):

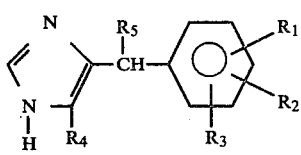

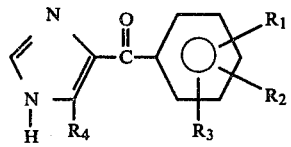

wherein $R_1$, $R_2$, $R_3$, $R_4$ and $R_5$ are as hereinbefore defined.

The compounds of the formula (I) are bases which form acid addition salts with both organic and inorganic acids. They thus form many pharmaceutically usable acid addition salts as, for instance, chlorides, bromides, sulfates, nitrates, phosphates, sulfonates, formates, tartrates, maleates, citrates, benzoates, salicylates, ascorbates and the like.

The present invention provides, for example, the following specific compounds of formula (I) wherein X is —$CH_2$—:
4-(2'-methylbenzyl)imidazole
4-(3'-methylbenzyl)imidazole
4-(4'-methylbenzyl)imidazole
4-(2'-methoxybenzyl)imidazole
4-(3'-methoxybenzyl)imidazole
4-(4'-methoxybenzyl)imidazole
4-(2'-ethylbenzyl)imidazole
4-(4'-ethylbenzyl)imidazole
4-(2'-chlorobenzyl)imidazole
4-(4'-chlorobenzyl)imidazole
4-(2',6'-dibromobenzyl)imidazole
4-(2'-bromobenzyl)imidazole
4-(2'-fluorobenzyl)imidazole
4-(2',6'-dichlorobenzyl)imidazole
4-(2',6'-difluorobenzyl)imidazole
4-(2',6'-dimethylbenzyl)imidazole
4-(2',3'-dimethylbenzyl)imidazole
4-(2',4'-dimethylbenzyl)imidazole
4-(3',4'-dimethylbenzyl)imidazole
4-(3',5'-dimethylbenzyl)imidazole
4-(2',6'-diethylbenzyl)imidazole
4-(2',4',6'-trimethylbenzyl)imidazole
4-(4'-amino-3',5'-dichlorobenzyl)imidazole
4-(3'-amino-2',6'-dimethylbenzyl)imidazole
5-methyl-4-(2'-methylbenzyl)imidazole
5-methyl-4-(2',3'-dimethylbenzyl)imidazole
4-(2',6'-dimethylbenzyl)-5-methylimidazole
4-(4'-amino-3',5'-dimethylbenzyl)-5-methylimidazole
4-(3',5'-dimethyl-4'-hydroxybenzyl)imidazole The present invention further provides the following specific compounds as exemplary of the compounds of formula (I) wherein X is —CHOH—:
5-methyl-4-(α-phenyl)hydroxymethylimidazole
5-methyl-4-(α-(2'-methylphenyl)]hydroxymethylimidazole
5-methyl-4-[α(2',6'-dimethylphenyl)]hydroxymethylimidazole
5-methyl-4-[α-(2',3'-dimethylphenyl)]hydroxymethylimidazole
4-(α-phenyl)hydroxymethylimidazole
4-[α-(2'-methylphenyl)]hydroxymethylimidazole
4-[α-(3'-methylphenyl)]hydroxymethylimidazole
4-[α-(4'-methylphenyl)]hydroxymethylimidazole
4-[α-(2'-methoxyphenyl)]hydroxymethylimidazole
4-[α-(3'-methoxyphenyl)]hydroxymethylimidazole
4-[α-(4'-methoxyphenyl)]hydroxymethylimidazole
4-[α-(2'-ethylphenyl)]hydroxymethylimidazole 4-[α-(4'-ethylphenyl)]hydroxymethylimidazole
4-[α-(2',6'-dimethylphenyl)]hydroxymethylimidazole
4-[α-(2',3'-dimethylphenyl)]hydroxymethylimidazole
4-[α-(2',4'-dimethylphenyl)]hydroxymethylimidazole
4-[α-(3',4'-dimethylphenyl)]hydroxymethylimidazole
4-[α-(3',5'-dimethylphenyl)]hydroxymethylimidazole
4-[α-(2',6'-diethylphenyl)]hydroxymethylimidazole
4-[α-(3'-amino-2',6'-dimethylphenyl)]hydroxymethylimidazole
4-[α-(4'-chlorophenyl)]hydroxymethylimidazole
4-[α-(2',4',6'-trimethylphenyl)]hydroxymethylimidazole The following compounds can be mentioned as specific examples of the compounds of formula (I) wherein X is —CHOR$_6$—:
4-(α-phenyl)ethoxymethylimidazole
4-[α-(2'methylphenyl)]methoxymethylimidazole
4-[α-(2'-methylphenyl)]ethoxymethylimidazole
4-[α-(3'-methylphenyl)]ethoxymethylimidazole
4-[α-(4'-methylphenyl)]ethoxymethylimidazole
4-[α-(2'-methoxyphenyl)]ethoxymethylimidazole
4-[α-(3'-methoxyphenyl)]ethoxymethylimidazole
4-[α-(4'-methoxyphenyl)]ethoxymethylimidazole
4-[α-(2',4',6'-trimethylphenyl)]ethoxymethylimidazole
4-[α-(2',6'-dimethylphenyl)]methoxymethylimidazole
4-[α-(2',6'-dimethylphenyl)]ethoxymethylimidazole
5-methyl-4-(α-phenyl)ethoxymethylimidazole
5-methyl-4-[α-(2',6'-dimethylphenyl)]methoxymethylimidazole
5-methyl-4-[α-(2',6'-dimethylphenyl)]ethoxymethylimidazole The following compounds are named as being illustrative of the 4-benzoylimidazoles of the invention, i.e., the compounds of formula (I) wherein X is —CO—:
4-(2'-methylbenzoyl)imidazole
4-(3'-methylbenzoyl)imidazole
4-(4'-methylbenzoyl)imidazole
4-(2'-methoxybenzoyl)imidazole
4-(3'-methoxybenzoyl)imidazole
4-(4'-methoxybenzoyl)imidazole
4-(2'-ethylbenzoyl)imidazole
4-(4'-chlorobenzoyl)imidazole
4-(2',6'-dimethylbenzoyl)imidazole
4-(2',3'-dimethylbenzoyl)imidazole
4-(2',4'-dimethylbenzoyl)imidazole
4-(3',5'-dimethylbenzoyl)imidazole
4-(3',4'-dimethylbenzoyl)imidazole
4-(2',4',6'-trimethylbenzoyl)imidazole
5-methyl-4-(2'-methylbenzoyl)imidazole
4-(2',6'-dimethylbenzoyl)-5-methylimidazole
4-(2',6'-dimethyl-3'-nitrobenzoyl)imidazole The compounds of formula (I), as free bases and as pharmaceutically acceptable salts thereof, have been found to possess many excellent pharmacological properties. Thus, the compounds of the invention exhibit excellent anti-ulcer properties. In addition, many of the compounds of the invention process excellent anti-hypertensive, diuretic, sedative, analgesic, anti-inflammatory and tranquilizing properties. (Preliminary tests have also shown that some compounds of the invention possess anti-convulsant, anti-depressant and anti-arrhythmic activity.) The positions and nature of the substitutents have been found to affect the relative strength of these pharmacological properties. This will be more apparent from the pharmacological test data set forth hereinbelow.

While all the compounds of formula (I) essentially satisfy the objectives of the present invention, certain groups of compounds remain preferred. One such preferred group can be represented by the structural formula:

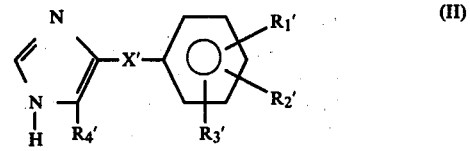

wherein X' is —CH$_2$—,

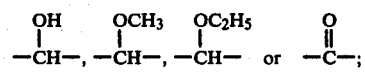

R'$_1$, R'$_2$ and R'$_3$, which can be the same or different, are each hydrogen, chloro, bromo, fluoro, hydroxy, methyl, ethyl or methoxy; and R'$_4$ is hydrogen or methyl. It is desirable for at least one of R$_1$, R$_2$ and R$_3$ to be other than hydrogen, and for the substituent or substituents on the benzene ring to be in the 2-, 3-, or 4-position, the 2,3-, 2,4- or 2,6-positions or in the 2,4,6-positions, especially preferred compounds of formula (II) having one, two or three identical substituents on the benzene ring selected from the group consisting of methyl, ethyl, methoxy and chloro in the indicated positions.

The present invention provides a number of advantageous processes for the preparation of the subject compounds. One especially desirable process is a Grignard reaction in which an imidazole of the formula:

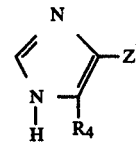

wherein R$_4$ is defined as before and Z is —CHO or —COOR, is reacted with a phenylmagnesium halide derivative of the formula:

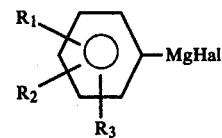

wherein R$_1$, R$_2$ and R$_3$ are defined as before. In the imidazole starting material, the —COOR radical can represent any ester grouping, for example, R can be selected from a wide variety of substituted and unsubstituted alkyl, aralkyl and aryl groups. When Z in the starting material is —CHO, the product is the corresponding compound of formula (I) wherein X is

when Z in the starting material is —COOR, the corresponding benzoyl derivative [i.e., the compound of formula (I) wherein X is

is obtained.

The phenylmagnesiumhalide derivative can be, for example, a phenylmagnesiumbromide derivative, which is prepared by reacting the corresponding bromobenzene derivative with magnesium. Suitable solvents for the reaction include a variety of ethers, preferably, tetrahydrofuran. The phenylmagnesiumhalide derivative is prepared in the usual way by adding the bromobenzene derivative in a suitable solvent, e.g., tetrahydrofuran, dropwise onto magnesium turnings covered by tetrahydrofuran, at the boiling point of the reaction mixture. When the magnesium turnings have reacted, the mixture is cooled slightly and the 4-imidazole derivative is added in solid form in small portions. After the addition, the reaction mixture is refluxed until all of the 4-imidazole derivative has reacted. The reaction time varies between one and five hours. In the reaction, at least two equivalents of phenylmagnesiumhalide are used per one equivalent of 4-imidazolealdehyde, because the last mentioned compound contains active hydrogen which binds a part of the Grignard reagent.

The above-described Grignard reaction utilizing a 4-imidazolealdehyde as starting material is a surprising and new method for the synthesis of imidazole derivatives. The process in surprising in view of the teachings of the prior art. Thus, for example, Deulofeu et al, *J. Org. Chem.* 14 (1949), 915 states that 4-imidazolealdehyde does not react with methylmagnesiumiodide, i.e., in the Grinard reaction.

Another process for the preparation of compounds of the present invention comprises reduction of a compound of formula:

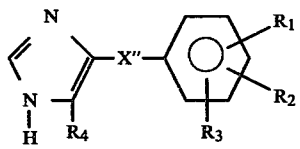

wherein $R_1$, $R_2$, $R_3$ and $R_4$ are defined as hereinabove and X''

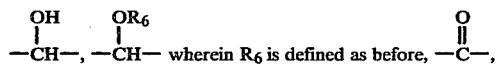

or

wherein $R_7$ is a hydrogenolysable group such as a halogen atom or a sulfonate radical. When X'' in the depicted starting material is

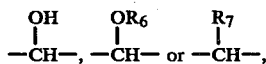

then X in the resultant product of formula (I) is —$CH_2$—. When the starting material is a benzoyl derivative, i.e. when X'' in the starting material is

then it is possible to obtain either the corresponding compound of formula (I) wherein X is

or the corresponding compund of formula (I) wherein X is —$CH_{12}$—. The reduction is preferably performed under acid conditions, in the presence of a catalyst and under a hydrogen atmosphere. Suitable solvents can be exemplified by water, alcohols (such as ethanol) and acetic acid. The solution is acidified by adding an appropriate acid, e.g., hydrochloric acid. Suitable catalysts are, for example, platinum oxide, palladium-on-carbon or Raney-nickel. The reaction is conveniently carried out at a temperature of 25°-70° C., with good stirring, although reaction conditions will of course vary depending on the nature of the desired derivative.

The compounds of formula (I) wherein X is

can be conveniently prepared by treatment of a corresponding compound of formula (I) wherein X is

with a compound of the formula $R_6OH$ in the presence of acid. Preferably, the imidazole starting material is simply refluxed in a suitable alcohol in the presence of an acid, suitable acids for this purpose being inorganic and organic acids, e.g., hydrochloric acid.

The compounds of formula (I) wherein X is

can also be prepared by oxidation of the corresponding compounds of formula (I) wherein X is

The oxidation is conveniently performed using nitric acid as the oxidizing agent, although other common oxidants can also be used. Typically, the imidazole starting material is dissolved in nitric acid and the reaction mixture is maintained at elevated temperature until the reaction is completed. If the treatment with nitric acid is of long duration and a large excess of acid is employed, nitration of the aromatic ring can occur at the same time.

An alternate route to the compounds of formula (I) wherein X is —$CH_2$— comprises reacting a 4-halomethylimidazole of the formula:

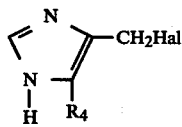

wherein R$_4$ is defined as before and Hal is a halogen atom, with a benzene derivative of the formula:

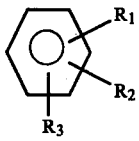

wherein R$_1$, R$_2$ and R$_3$ are defined as before. Typically, the alkylation proceeds by contacting the imidazole, e.g., 4-chloromethylimidazole, with the benzene derivative, with stirring, at an elevated temperature. Suitable solvents for use in this process include alcohols and aromatic hydrocarbons (e.g., xylene). The imidazole derivative can be employed in the form of an acid addition salt (e.g., the hydrochloride), in which case an equivalent amount of an appropriate base such as sodium carbonate is added. If the benzene derivative is a base, e.g., 2,6-dichloroaniline, then two equivalents thereof are employed per one equivalent of imidazole derivative.

Yet another process for the preparation of the compounds of formula (I) wherein X is —CH$_2$— comprises reacting a benzene derivative of the formula:

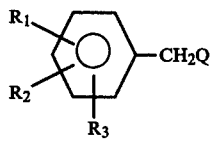

wherein R$_1$, R$_2$ and R$_3$ are defined as hereinabove and Q is a radical selected from the group consisting of

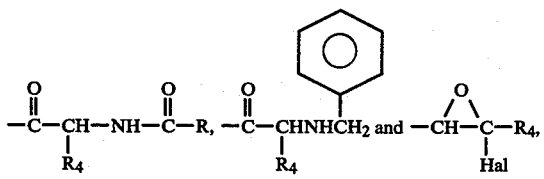

wherein R, R$_4$ and Hal are defined as hereinabove, with formamide. Preferably the reaction is performed by vigorously boiling the benzene derivative in formamide, the reaction time varying with the particular material employed. Reaction times typically are from 30 minutes to 8 hours. Of course, the formamide treatment will be followed by reaction with an appropriate acid (e.g. HCl) when Q in the starting material is

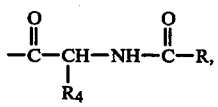

in order to obtain the corresponding compound of formula (I) wherein X is —CH$_2$—. Similarly, when a starting material wherein Q is

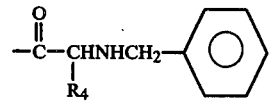

is employed, then the formamide treatment will be followed by hydrogenation, thus affording the desired compound of formula (I).

A further process for the preparation of the subject compounds wherein X is —CH$_2$— comprises hydrolysis of the corresponding compounds of the formula:

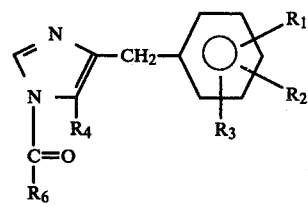

wherein R$_1$, R$_2$, R$_3$, R$_4$ and R$_6$ are defined as before. Preferably, the hydrolysis are carried out by boiling the starting material, an N-acetylated imidazole derivative, in an aqueous solution of an inorganic acid until the reaction is completed.

Yet another process for the preparation of the compounds of formula (I) wherein X is —CH$_2$— comprises hydrogenation of a starting material selected from the group consisting of:

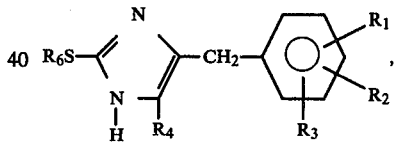

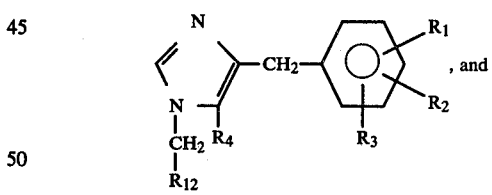

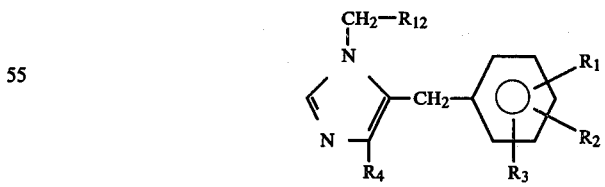

wherein R$_1$, R$_2$, R$_3$, R$_4$ and R$_6$ are defined as before and R$_{12}$ is an aryl group. The hydrogenation is conveniently conducted in the presence of a suitable catalyst and under a hydrogen atmosphere, with stirring. Suitable catalysts include platinum oxide, palladium-on-carbon and Raney nickel. Reaction temperatures vary with the particular starting material employed, with typical temperatures being 25°-70° C.

The present invention further provides yet another process for preparing certain select compounds of the invention. Thus, according to this embodiment of the invention, a starting material of the formula:

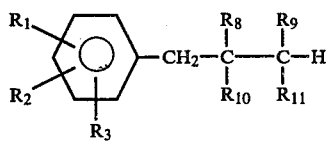 (III)

wherein $R_1$, $R_2$ and $R_3$ are as hereinbefore defined; and wherein $R_8$, $R_9$, $R_{10}$ and $R_{11}$, which can be the same or different, are each hydrogen, hydroxy, halogen, amino, —O— alkyl or

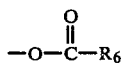

wherein $R_6$ is defined as before; or wherein $R_8$ and $R_{10}$ can be combined to form a keto group, or $R_9$ and $R_{11}$ can be combined to form a keto group, or both $R_8$ and $R_{10}$ and $R_9$ and $R_{11}$ can simultaneously form keto groups; is reacted with a reagent capable of converting said starting material to an imidazole of the formula:

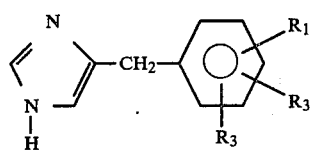

wherein $R_1$, $R_2$ and $R_3$ are defined as before. Reagents capable of converting the depicted starting material to the corresponding imidazole include $NH_3 + CH_2O$ (or a source of ammonia and formaldehyde); $HN=CH-NH_2$;

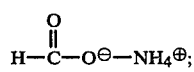

and $HCONH_2$ (formamide). Choice of an appropriate reagent varies with the particular starting material employed. For instance, when the starting material is a haloketone or a haloaldehyde, for example, when $R_8$ and $R_{10}$ together form a keto group, $R_9$ is bromine and $R_{11}$ is hydrogen, or when $R_9$ and $R_{11}$ form a keto group, $R_8$ is bromine and $R_{10}$ is hydrogen, then it is preferable to react the starting material with formamide in order to obtain the 4-benzylimidazole derivative. It is likewise preferable to employ formamide as the reagent in cases where, in place of the bromine atom in the aformentioned starting materials, there is instead a hydroxyl, amino or acetyl group. In these instances, formamide is used in excess and acts in part as the solvent. Generally, the reaction is run at the boiling point of formamide for a period of time ranging from one to five hours. If the starting material is a glyoxal derivative, e.g., benzyl glyoxal or other compound of the type:

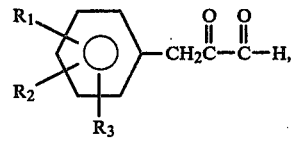

then the ammonia needed for the synthesis of the imidazole ring is suitably taken from ammonium acetate, while the needed formalin is taken from hexamethylenetetramine. Two equivalents of these reagents are used per equivalent of glyoxal derivative. Suitable solvents are, for example, dimethylformamide and formamide. Typically, the reaction temperature is the boiling point of the reaction mixture, and the reaction time is usually from one to three hours. Alternatively, the glyoxal derivative can be reacted directly with ammonia and formaldehyde, or with formamide, but the yields of desired product are generally lower.

A surprising aspect of the abovementioned reaction is the fact that the hydroxyacetal starting materials, e.g., compounds of the formula:

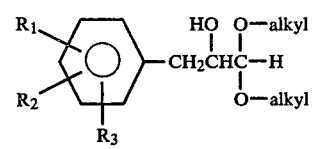

very readily react with formamide to form the corresponding imidazoles.

As a variation of the above-described process, a starting material of formula (III) can be treated with an appropriate reagent, particularly formamide, under milder conditions than those discussed above, allowing isolation of the intermediate oxazole, which can then be further reacted with formamide to afford the corresponding compound of formula (I). In this variation, the first formamide treatment is carried out at a low temperature (80°–120° C., depending on the particular starting material employed), to afford a novel oxazole of the formula:

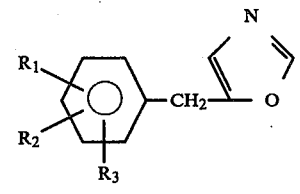

or

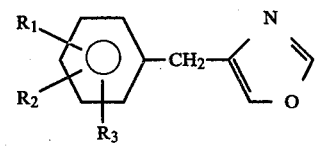

which can then be easily reacted with formamide, typically at about 180° C., for about 4 hours, to afford the desired compound of the present invention. Preliminary testing has indicated that the novel oxazole intermediates also display valuable pharmacological properties, i.e., they exhibit anti-hypertensive activity.

The starting materials of formula (III) can be prepared by known methods. Reference is made to Examples 49(a), (b) and (c) and 50(a) set forth hereinafter for a description of methods which have been employed to prepare various starting materials of formula (III), it being understood that such examples are simply illustrative of procedures which can be utilized to prepare the desired starting materials.

As stated hereinabove, the compounds of the general formula (I) and their non-toxic, pharmaceutically acceptable acid addition salts have valuable pharmacological properties and have been found to possess excellent anti-hypertensive, anti-ulcer, diuretic, sedative, analgesic, anti-inflammatory and tranquilizing activity in mammals.

The compounds of formula (I), their non-toxic, pharmaceutically acceptable acid addition salts or mixtures thereof may be administered parenterally, intravenously or orally. Typically, an effective amount of the derivative is combined with a suitable pharmaceutical carrier. As used herein, the term "effective amount" encompasses those amounts which yield the desired activity without causing adverse side-effects. The precise amount employed in a particular situation is dependent upon numerous factors such as method of administration, type of mammal, condition for which the derivative is administered, etc., and of course the structure of the derivative. One of the most potent anti-hypertensive derivatives of the invention is 4-(2',6'-dimethylbenzyl)imidazole, the daily dose of which generally ranges from about 0.01-0.05 milligrams per kilogram of mammal.

The pharmaceutical carriers which are typically employed with the derivatives of the present invention may be solid or liquid and are generally selected dependent on the planned manner of administration. Thus, for example, solid carriers include lactose, sucrose, gelatin and agar, while liquid carriers include water, syrup, peanut oil and olive oil. Other suitable carriers are well-known to those skilled in the art of pharmaceutical formulations. The combination of the derivative and the carrier may be fashioned into numerous acceptable forms, such as tablets, capsules, suppositories, solutions, emulsions, and powders.

The anti-hypertensive properties of the imidazole derivatives of the present invention have been determined according to the following procedure. Sprague-Dawley rats of normal weight were first anesthetized with urethane. After this, the femoral artery was connected by way of a polyethylene tube with a blood pressure transducer. The test substance was then injected into the femoral vein and the blood pressure and the pulse frequency were registered with a recorder. The minimum doses producing a significant change were found, i.e. ± at least 20% in the case of blood pressure, and ± at least 3% in the case of pulse frequency.

In a further test for anti-hypertensive properties, unanesthetized Okamoto-Aoki spontaneous hypertensive rats (SHR) were used. The test derivative was administered perorally by way of a tube into the stomach. The blood pressure was measured from the tail using an indirect bloodless method.

The preventive effect on the formation of ulcers of the compounds of formula (I) has been tested in the following manner. Female Sprague-Dawley rats, approximately ten weeks old and weighing 200-250 g. each, were fasted overnight. The rats were divided into two groups. The rats in one group were given only 20 mg/kg p.o. of indomethacin, while the rats in the other group were given the test compound by i.p. administration simultaneously with the indomethacin administration. The rats were killed after 4 hours and the anti-ulcer effect was estimated by counting the ulcers and comparing the number of them in the rats receiving test compound to the number of ulcers found by induction with indomethacin.

The diuretic activity of the compounds of the invention was studied in rats by collecting the urine output during 0-5 hours after i.p. injection of the compounds. Before the test, the animals were fasted overnight, then were given 10 ml of water p.o. immediately before the injection.

The sedative potency of the compounds was evaluated by the following tests:

(1) The sleeping time of male chickens (1-5 days old) was studied after administration of the test substances i.m. into two animals per dose level (Delbarre and Schmitt, *Eur. J. Pharmacol*, 22:355, 1973).

(2) Potentiation of barbiturate sleeping time was studied in mice. The compound examined was given i.p. 30 minutes before the pentobarbitone (60 mg/kg i.p.).

(3) Spontaneous motility of mice and rats was measured using the Animex-activity meter. The test compounds were administered i.p. 30 minutes before the measuring periods of two minutes.

The analgesic activity of the compounds of formula (I) was tested in the following manner:

(1) Writhing test

The compounds studied and saline were administered p.o. to rats. Forty-five minutes later, 1 ml of 1% acetic acid was administered i.p. The number of writhes was recorded in the following 25 minute period (Koster et al: Fed. Proc. 18:412, 1959).

(2) Hot Plate Test

Test compounds or saline were given i.p. to male mice. Thirty minutes thereafter, the time for which the mice remained on a 55° C. plate was recorded. The results are expressed as compared to saline.

The anti-inflammatory activity of the compounds of the invention was determined by inhibition of the carrageenan induced oedema in rats by the compounds examined (Winter C. A. et al., *Proc. Soc. Exp. Biol. Med.* 111:544, 1962).

The tranquilizing activity of the compounds was determined by the following methods:

(1) Irwin screen in rats (Irwin S., *Psychopharmacologia* 13:222, 1968)

Especially sedatory and cataleptic activity and effects on muscle tone are observed.

(2) Tranquilizing or taming effect on cattle:

The test compounds were administered i.m. to cattle, mostly to heifers (150-200 kg). The animals were observed for 3 hours: especially the vital functions, reaction to pain and handling, muscle tone, possible sleep etc.

The most suitable tranquilized state of an animal includes the ability to retain the upright position and coordination with minimal avoidance reactions to painful stimuli and handling. Thus, a combination of sedative and analgesic potency is required.

Acute toxicity was determined by using female mice of NMRI-Strain with an age of about 7 months and weighing 30-40 g. The administration of the test compound was i.v.

Some examples of the pharmacological properties of the compounds of the invention are as follows:

4-(2',6'-Dimethylbenzyl)imidazole, which has a $LD_{50}$ value of 40 mg/kg i.v., was found in the blood pressure study with anesthetized rats of normal weight described above to cause a detectable lowering of the blood pressure even with a dose of 1 µg/kg i.v. With a dose of 3 µg/kg i.v., the blood pressure lowering was quite clear and with a dose of 10 µg/kg i.v. the reduction of blood pressure was on an average 30%, the decrease of pulse frequency being 12% on an average. The duration of the effect was at least 50 minutes (after which time the determination was interrupted). As the $LD_{50}$ is 40 mg/kg i.v. in mice, it can be concluded that the therapeutic range is very broad. When the antihypertensive effect of the compound was determined with awake SHR-rats, it was found that the decrease of blood pressure was about 20% with a dose of 100 µg/kg p.o. and 25% with a dose of 300 µg/kg p.o. four hours after the administration. When the anti-ulcer effect of the compound was determined in the manner described above, it was found that a dose of 5 µg/kg i.p. completely prevented the formation of ulcers.

For the compound 4-(2'-methylbenzyl)imidazole, having a $LD_{50}$ of 25 mg/kg i.v. in mice, the following results in the above-mentioned tests were obtained: lowering of blood pressure with a dose of 0.5 mg/kg i.v. of 10%, 30 minutes after administration; complete prevention of the formation of ulcers at a dose of 5 µg/kg i.p.

The compound of 4-[α-(2',6'-dimethylphenyl)]hydroxymethylimidazole, having a $LD_{50}$ of 125 mg/kg i.v. in mice, gave the following results in the above-mentioned tests: A lowering of blood pressure with a dose of 300 µg/kg i.v. was noticeable; with a dose of 3 mg/kg p.o. with awake SHR rats, the decrease was 20% 3 hours after administration. With a dose of 5 mg/kg, the compound completely prevented the formation of ulcers, while with a dose of 0.5 mg/kg, the prevention was partial.

When 4-[α-(2'-methylphenyl)]hydroxymethylimidazole, having a $LD_{50}$ of 160 mg/kg i.v. in mice, was tested as above, no anti-hypertensive effect was found. On the other hand, a dose of 5 mg/kg completely prevented the formation of ulcers and a dose of 0.5 mg/kg prevented them partly.

When 5-methyl-4-(2',6'-dimethylbenzyl)imidazole, having a $LD_{50}$ of 27 mg/kg i.v. in mice, was tested as above, no anti-hypertensive effect was found. A dose of 0.5 mg/kg partly prevented the formation of ulcers and the dose 5 mg/kg prevented them completely.

When 4-(2',6'-dimethylbenzoyl)imidazole, having a $LD_{50}$ of over 100 mg/kg i.v. in mice, was tested as above, only a very slight anti-hypertensive effect was found. A dose of 20 mg/kg prevented completely the formation of ulcers, while 10 mg/kg prevented them partially.

When 4-[α-(2',6'-dimethylphenyl)ethoxymethylimidazole, having a $LD_{50}$ of 45 mg/kg i.v. in mice, was tested, it possessed only a very slight anti-hypertensive effect. However, a dose of 5 mg/kg completely prevented the formation of ulcers, while 0.5 mg/kg prevented them partly.

A summary of the pharmacological properties of the compounds of the invention is given in the following Tables. In the Tables, + means having a moderate effect and ++ means having a marked effect.

| EXAMPLES OF COMPOUNDS WITH ANTI-HYPERTENSIVE EFFECTS | |
|---|---|
| | Blood Pressure Minimum Dose (mg/kg i.v.) having a significant lowering effect |
| 4-(2',6'-dimethylbenzyl)imidazole | 0.003–0.1 |
| 4-(2',3'-dimethylbenzyl)imidazole | 0.01–0.1 |
| 4-(2'-methylbenzyl)imidazole | 0.01–0.1 |
| 4-(2',6'-dichlorobenzyl)imidazole | 0.03–0.1 |
| 4-[α-(2',6'-dimethylphenyl)]-hydroxymethylimidazole | 0.1–3 |
| 4-[α-(2'-methoxyphenyl)]-hydroxymethylimidazole | 0.3–1 |
| 4-(2',6'-diethylbenzyl)imidazole | 0.03–0.2 |
| 4-[α-(2',6'-diethylphenyl)]hydroxy-methylimidazole | 0.3–1 |
| 4-(2',4',6'-trimethylbenzyl)-imidazole | 0.05–0.2 |

| | Pulse frequency Minimum Dose (mg/kg i.v.) having a significant | |
|---|---|---|
| | lowering effect | increasing effect |
| 4-(2',6'-dimethylbenzyl)-imidazole | 0.003 | — |
| 4-(2',3'-dimethylbenzyl)-imidazole | 0.01–1 | 3–10 |
| 4-(2'-methylbenzyl)-imidazole | 0.1–1 | — |
| 4-(2',6'-dichlorobenzyl)-imidazole | 0.03–0.1 | — |
| 4-[α-(2',6'-dimethyl-phenyl)]hydroxymethyl-imidazole | 0.1 | — |
| 4-[α-(2'-methoxyphenyl)]-hydroxymethylimidazole | 1 | — |
| 4-(2',6'-diethylbenzyl)-imidazole | 0.03 | |
| 4-[α-2',6'-diethyl-phenyl)]hydroxymethyl-imidazole | 0.3–1 | |
| 4-(2',4',6'-trimethyl-benzyl)imidazole | 0.03 | |

| EXAMPLES OF COMPOUNDS WITH A HIGH THERAPEUTIC INDEX FOR TREATMENT OF ULCEROUS CONDITIONS | | | |
|---|---|---|---|
| | Dosage (mg/kg) | | |
| | $LD_{50}$ (mouse, i.v.) | $ED_{50}$ | Therapeutic Index |
| 4-(2',6'-dimethyl-benzyl)imidazole | 40 | 0.005 | 8000 |
| 4-(2',3'-dimethyl-benzyl)imidazole | 35 | 0.005 | 7000 |
| 4-(2',4'-dimethyl-benzyl)imidazole | 65 | 0.03 | 2167 |
| 4-(2'-ethylbenzyl)-imidazole | 34 | 0.005 | 6800 |
| 4-(2'-methylbenzyl)-imidazole | 25 | 0.005 | 5000 |
| 4-(3'-methylbenzyl)-imidazole | 38 | 0.02 | 1900 |
| 4-(2',4',6'-trimethyl-benzyl)imidazole | 63 | 0.03 | 2100 |
| 4-(2'-chlorobenzyl)-imidazole | 65 | 0.03 | 2167 |
| 4-(2',6'-dichloro-benzyl)imidazole | 48 | 0.03 | 1600 |

EXAMPLES OF COMPOUNDS WITH DIURETIC EFFECT

| | Dosage (mg/kg) | Diuretic Effect(%) 2.5h | 5h |
|---|---|---|---|
| 4-[α-(2',3'-dimethylphenyl)]-hydroxymethylimidazole | 10.0 | 411 | 280 |
| | 0.6 | 160 | |
| | 0.15 | 145 | |
| 4-[α-(2',6'-dimethylphenyl)]-hydroxymethylimidazole | 30.0 | 121 | 66 |
| | 0.5 | 150 | |
| 4-[α-(2'-ethylphenyl)]-hydroxymethylimidazole | 30.0 | 234 | 211 |
| 4-[α-(2'-methoxyphenyl)]-hydroxymethylimidazole | 30.0 | 158 | 68 |
| 4-(2',4'-dimethylbenzyl)-imidazole | 0.5 | | 50 |
| | 30.0 | 228 | 181 |
| 4-(2',3'-dimethylbenzyl)-imidazole | 0.05 | 150 | |
| 4-(2',6'-dimethylbenzyl)-imidazole | 0.05 | 150 | |
| 4-(2'-methylbenzyl)-imidazole | 30.0 | 128 | 49 |
| | 0.05 | 100 | |
| 4-[α-(2',6'-dimethylphenyl)]-ethoxymethylimidazole | 30.0 | 60 | 16 |
| 4-(4'-methylbenzyl)imidazole | 0.5 | 50 | |
| 4-(2'-chlorobenzyl)imidazole | 0.5 | 50 | |
| 4-(2',4',6'-trimethylbenzyl)imidazole | 0.5 | 150 | |
| 4-(3'-methylbenzyl)imidazole | 0.5 | 100 | |

EXAMPLES OF COMPOUNDS WITH SEDATIVE EFFECT

| | Dosage (mg) | | |
|---|---|---|---|
| | 0.3–1.0 | 3–10 | 30–60 |
| 4-(2',4'-dimethylbenzyl)-imidazole | ++ | | |
| 4-(2',3'-dimethylbenzyl)-imidazole | ++ | | |
| 4-(3'-methylbenzyl)imidazole | | + | |
| 4-(2',4',6'-trimethylbenzyl)-imidazole | ++ | | |
| 4-(2'-ethylbenzyl)imidazole | ++ | | |
| 4-(3'-methoxybenzyl)imidazole | | + | |
| 4-(2'-chlorobenzyl)imidazole | ++ | | |
| 4-[α-(2',3'-dimethylphenyl)]-hydroxymethylimidazole | ++ | | |
| 4-[α-(2'-methoxyphenyl)]-hydroxymethylimidazole | | | ++ |
| 5-methyl-4-(2',6'-dimethylbenzyl)imidazole | | | + |

EXAMPLES OF COMPOUNDS WITH ANALGESIC EFFECT

| | Analgesic activity | | |
|---|---|---|---|
| | method and dosage (mg/kg) | increase in HP-time (%) W-number[1] | activity |
| 4-(3'-methylbenzyl)imidazole | HP 1.5 | 50 | |
| | W 30 | 0 | ++ |
| 4-(2',3'-dimethylbenzyl)imidazole | HP 0.6 | 200 | + |
| 4-(2',4'-dimethylbenzyl)-imidazole | W 100 | 0 | ++ |
| | HP 1.5 | 200 | + |
| 4-(2'-methylbenzyl)-imidazole | HP 1.5 | 200 | + |
| 4-(2'-chlorobenzyl)-imidazole | HP 1.5 | 200 | + |
| 4-[α-(2',4'-dimethylphenyl)]hydroxymethyl-imidazole | W 100 | 1.3 | + |
| | HP 1.5 | — | |
| 4-[α-(2',3'-dimethylphenyl)]hydroxymethylimidazole | W 100 | 0 | ++ |
| | HP 1.5 | 400 | ++ |
| 4-[α-(2'-methylphenyl)]-hydroxymethylimidazole | W 100 | 0 | ++ |
| 4-[α-(3'-methylphenyl)]-hydroxymethylimidazole | W 100 | 0 | ++ |
| 4-[α-(4'-methylphenyl)]-hydroxymethylimidazole | W 100 | 0.6 | ++ |
| 4-[α-(2'-ethylphenyl)]-hydroxymethylimidazole | W 100 | 0 | ++ |
| | HP 1.5 | 300 | + |
| 4-(2'-ethylbenzyl)imidazole | HP 1.5 | 150 | + |
| 4-[α-(2'-methoxyphenyl)]-hydroxymethylimidazole | W 100 | 2.5 | + |
| 4-[α-(3'-methoxyphenyl)]-hydroxymethylimidazole | W 100 | 0 | ++ |
| 4-[α-(4'-methoxyphenyl)]-hydroxymethylimidazole | W 100 | 1.9 | + |
| | HP 1.5 | — | |
| 4-[α-(2',6'-dimethylphenyl)]methoxymethyl-imidazole | W 100 | 13 | + |
| 4-[α-(2',6'-dimethylphenyl)]ethoxymethyl-imidazole | W 100 | 0.6 | ++ |
| 5-methyl-4-(2'-methyl-benzyl)imidazole | W 30 | 43 | + |
| 5-methyl-4-[α-(2',6'-dimethylphenyl)]-hydroxymethylimidazole | W 100 | 13 | + |

[1]HP = hot plate test
W = writhing test

EXAMPLES OF COMPOUNDS WITH ANTI-INFLAMMATORY EFFECTS

| | Anti-inflammatory activity at 100 mg/kg p.o. in the rat | |
|---|---|---|
| | inhibition carrageenan-induced oedema (%) | activity |
| 4-(2',4'-dimethylbenzyl)-imidazole | 76 | ++ |
| 4-(3'-methylbenzyl)-imidazole | 61 | + |
| 4-[α-(2',3'-dimethylphenyl)]-hydroxymethylimidazole | 52 | + |
| 4-[α-(2'-methylphenyl)]-hydroxymethylimidazole | 41 | + |
| 4-[α-(3'-methylphenyl)]-hydroxymethylimidazole | 34 | + |
| 4-[α(4'-methylphenyl)]-hydroxymethylimidazole | 38 | + |
| 4-[α-(2-ethylphenyl)]-hydroxymethylimidazole | 73 | ++ |
| 4-[α-(2'-methoxyphenyl)]-hydroxymethylimidazole | 69 | ++ |
| 4-[α-(3'-methyoxyphenyl)]-hydroxymethylimidazole | 71 | ++ |
| 4-[α(2',6'-dimethylphenyl)]-methoxymethylimidazole | 40 | + |
| 4-[α-(2',6'-dimethylphenyl)]-ethoxymethylimidazole | 35 | + |
| 4-[4'-methylbenzoyl)imidazole | 40 | + |
| 5-methyl-4-(2'-methylbenzyl)-imidazole | 44 | + |
| 5-methyl-4-[α(2',6'-dimethylphenyl)]hydroxy-methylimidazole | 52 | + |
| 5-methyl-4-[α-(2'-methyl-phenyl)]hydroxymethyl-imidazole | 67 | + |
| 5-methyl-4-(2'-methyl-benzoyl)imidazole | 44 | + |

EXAMPLES OF COMPOUNDS WITH TRANQUILIZING EFFECTS

| | Activity in rats | | |
|---|---|---|---|
| | dose (mg/kg) | decrease of motility | loss of muscle tone | catalepsia |
| 4-(2',3'-dimethylbenzyl)imidazole | 1.0 | + | + | − |
| 4-(2'-chlorobenzyl)imidazole | 0.25 | + | − | + |
| 4-(2',4',6'-trimethylbenzyl)imidazole | 1.0 | ++ | − | + |
| 4-(2',6'-dimethylbenzyl)imidazole | 1.0 | ++ | + | − |
| 4-(3'-methylbenzyl)imidazole | 1.0 | +− | − | |

| | Activity in cattle | | |
|---|---|---|---|
| | dose mg/kg | loss of avoidance | loss of muscle tone |
| 4-(2',3'-dimethylbenzyl)imidazole | 0.1 | ++ | − |
| 4-(2'-chlorobenzyl)imidazole | 0.1 | + | − |
| 4-(2',4',6'-trimethylbenzyl)imidazole | 0.1 | + | + |
| 4-(2',6'-dimethylbenzyl)imidazole | 0.05 | ++ | + |
| 4-(3'-methylbenzyl)imidazole | 0.1 | + | − |

Based on testing conducted thus far, the following clinical dosage ranges for the compounds of the invention have been estimated for oral administration: anti-ulcer agents, 0.1 to 10.0 mg/day; anti-hypertensive agents, 0.1 to 10.0 mg/day; anti-inflammatory agents, 10.0 to 1000 mg/day; analgesic agents, 10.0 to 1000 mg/day; diuretic agents, 1.0 to 100 mg/day; and sedative agents, 1.0 to 100 mg/day.

The invention will appear more fully from the following examples. These examples are given by way of illustration only and are not to be construed as limiting the invention in spirit or in scope as many modifications in materials and methods will be apparent to those skilled in the art.

In these examples, where $1_H$-NMR spectrum shifts are presented, the NMR spectra were determined with a Perkin Elmer R 24 apparatus using an external tetramethylsilane standard, from which the presented chemical shifts (δ,ppm) are tabulated. The letters s, d, t and m are used to indicate a singlet, doublet, triplet or multiplet, respectively. In the same connection, the number of hydrogen atoms is also stated. The compounds which are indicated as bases are tested in deuterium methanol, deuterium acetone or deuterium chloroform, while the values for compounds which are indicated as hydrochlorides were determined in deuterium oxide. Unless otherwise specified the NMR values given below are for $1_H$-NMR spectrum shifts.

The mass-spectra were determined with a Perkin-Elmer RMU apparatus using direct inlet system. The temperature employed was the lowest temperature needed for the evaporation of the compound as base. In the examples the strongest and the most essential fragment-ions from a structural viewpoint are given as m/e values. In parenthesis is given the intensity of the fragmentation in relation to the main peak.

EXAMPLE 1

4-[α-(2'-Methylphenyl)]hydroxymethylimidazole 4.8 g of dry magnesium turnings are covered with 100 ml of dry tetrahydrofuran (THF). The mixture is heated to boiling and a solution of 2-bromotoluene in 50 ml of dry tetrahydrofuran is added dropwise at such a rate that gentle refluxing is maintained. After the addition is complete, the reaction mixture is refluxed for an additional 30 minutes. The reaction mixture is cooled to 50° C. and 9.6 g of 4-imidazolealdehyde are added slowly in small portions. After the addition is complete, the mixture is refluxed for 4 hours. Then, the reaction mixture is cooled and poured into 100 ml of cold water containing 20 ml of concentrated hydrochloric acid. Part of the tetrahydrofuran is distilled to give a smaller volume and the tetrahydrofuran is replaced with water. The mixture is washed twice with 50 ml portions of chloroform. The aqueous layer is made alkaline with sodium hydroxide solution (pH about 8). The precipitate which forms is washed with water and dried. The crude product is recrystallized from a mixture of water and ethanol to give a product melting at 163°–164° C.

NMR: 1.9 (s, 3H), 4.85 (s, 2H), 5.7 (s, 1H), 6.35 (s, 1H), 6.85 (m, 3H), 7.3 (m, 2H).

MS: 188 (37%), 171 (14%), 170 (98%), 169 (100%), 155 (12%), 143 (28%), 142 (19%), 116 (19%), 115 (29%), 97 (21%), 95 (27%), 91 (21%), 69 (26%).

EXAMPLE 2

4-[α-(2',6'-Dimethylphenyl)]hydroxymethylimidazole

The procedure of Example 1 is repeated except that 1-bromo-2,6-dimethylbenzene is used in place of 2-bromotoluene. The product, after recrystallization from ethanol, melts at 166°–167° C.

NMR: 2.0 (s, 6H), 4.7 (s, 2H), 5.95 (s, 1H), 6.3 (s, 1H), 6.7 (s, 3H), 7.25 (s, 1H).

MS: 202 (60%), 187 (14%), 184 (100%), 183 (96%), 169 (38%), 157 (18%), 156 (25%), 134 (16%), 133 (20%), 115 (18%), 105 (18%), 97 (32%), 95 (40%), 91 (24%), 77 (16%), 69 (50%).

EXAMPLE 3

4-(α-Phenyl)hydroxymethylimidazole

The procedure of Example 1 is repeated, except that bromobenzene is used in place of 2-bromotoluene. The product is converted to its hydrochloride in isopropanol. The hydrochloride, after recrystallization from isopropanol, melts at 130°–132° C.

NMR: (HCL salt) 4.9 (s, 3H), 5.95 (s, 1H), 7.2 (s, 1H), 7.4 (s, 5H), 8.4 (s, 1H).

MS: 174 (100%), 157 (22%), 156 (17%), 130 (25%), 129 (46%), 104 (17%), 103 (14%), 102 (20%), 97 (86%), 96 (82%), 95 (89%), 91 (93%), 78 (26%), 77 (57%), 69 (86%), 68 (78%).

EXAMPLE 4

4-[α-(3'-Methylphenyl)]hydroxymethylimidazole

The procedure of Example 1 is repeated, except that 3-bromotoluene is used. The product melts at 120°–122° C.

NMR: 1.85 (s, 3H), 4.15 (s, 2H), 5.3 (s, 1H), 6.35 (s, 1H), 6.75 (m, 4H), 7.2 (s, 1H).

MS: 188 (100%), 187 (29%), 171 (21%), 170 (30%), 144 (17%), 143 (40%), 115 (16%), 97 (63%), 96 (67%), 95 (73%), 91 (33%), 69 (49%), 68 (51%).

EXAMPLE 5

4-[α-(4'-Methylphenyl)]hydroxymethylimidazole

The procedure of Example 1 is repeated, except that 4-bromotoluene is used. The product, after recrystallization from a water-ethanol mixture, melts at 116°–119° C.

NMR: 2.25 (s, 3H), 5.6 (s, 2H), 5.75 (s, 1H), 6.75 (2, 1H), 7.2 (m, 5H).

MS: 188 (100%), 171 (36%), 170 (50%), 155 (14%), 143 (48%), 97 (49%), 96 (88%), 95 (98%), 91 (43%), 69 (56%), 68 (68%).

EXAMPLE 6

4-[α-(2',4'-Dimethylphenyl)]hydroxymethylimidazole

The procedure of Example 1 is repeated, except that 1-bromo-2,4-dimethylbenzene is used. The crude product thus obtained is recrystallized from a water-ethanol mixture to give a product melting at 115°–120° C.

NMR: 2.0 (s, 3H), 2.1 (s, 3H), 4.95 (s, 2H), 5.8 (s, 1H), 6.95 (s, 1H), 6.8 (m, 2H), 7.2 (m, 1H), 7.4 (s, 1H).

MS: 202 (62%), 185 (25%), 184 (100%), 183 (73%), 169 (39%), 157 (23%), 156 (24%), 133 (13%), 130 (13%), 115 (15%), 105 (11%), 97 (12%), 95 (44%), 91 (26%), 77 (14%), 69 (33%).

EXAMPLE 7

4-[α-(2',3'-Dimethylphenyl)]hydroxymethylimidazole

The procedure of Example 1 is repeated, except that 1-bromo-2,3-dimethylbenzene is used. The melting point of the product, after recrystallization from water-ethanol, is 140°–142° C.

NMR: 1.75 (s, 3H), 1.85 (s, 3H), 4.75 (s, 2H), 5.65 (s, 1H), 6.25 (s, 1H), 6.85 (m, 3H), 7.2 (s, 1H).

EXAMPLE 8

4-[α-(3',4'-Dimethylphenyl)]hydroxymethylimidazole

The procedure of Example 1 is repeated, except that 1-bromo-3,4-dimethylbenzene is used.

NMR: 1.85 (s, 6H), 4.8 (s, 2H), 5.4 (s, 1H), 6.6 (m, 4H), 7.2 (s, 1H).

EXAMPLE 9

4-[α-(2'-Methoxyphenyl)]hydroxymethylimidazole

The procedure of Example 1 is repeated, except that 1-bromo-2-methoxybenzene is used. The product is transformed to the hydrochloride in isopropanol. The melting point of the hydrochloride is 166°–168° C.

NMR (HCl salt): 3.65 (s, 3H), 4.7 (s, 3H), 6.1 (1H), 7.1 (m, 5H), 8.5 (s, 1H).

EXAMPLE 10

4-[α-(3'-Methoxyphenyl)]hydroxymethylimidazole

The procedure of Example 1 is repeated, except that 1-bromo-3-methoxybenzene is used. After recrystallization from a water-ethanol mixture, the product melts at 96°–97° C.

NMR: 3.75 (s, 3H), 5.1 (s, 2H), 5.75 (s, 1H), 7.0 (m, 5H), 7.55 (s, 1H).

EXAMPLE 11

4-[α-(4'-Methoxyphenyl)]hydroxymethylimidazole

The procedure of Example 1 is repeated, except that 1-bromo-4-methoxybenzene is used. The product melts at 127°–129° C.

NMR: 3.7 (s, 3H), 5.25 (s, 2H), 5.75 (s, 1H), 7.1 (m, 5H), 7.55 (s, 1H).

EXAMPLE 12

4-[α-(4'-Chlorophenyl)]hydroxymethylimidazole

The procedure of Example 1 is repeated, except that 1-bromo-4-chlorobenzene is used. After recrystallization from water-ethanol, the product melts at 159°–160° C.

NMR: 4.75 (s, 2H), 5.45 (s, 1H), 6.5 (s, 1H), 7.0 (s, 4H), 7.25 (s, 1H).

EXAMPLE 13

4-[α-(2'-Ethylphenyl)]hydroxymethylimidazole

The procedure of Example 1 is repeated, except that 1-bromo-2-ethylbenzene is used. After recrystallization from water-ethanol, the product melts at 139°–142° C.

NMR: 1.1 (t, 3H), 2.65 (q, 2H), 5.05 (s, 2H), 6.05 (s, 1H), 6.65 (s, 1H), 17.3 (m, 4H), 7.55 (s, 1H).

EXAMPLE 14

4-[α-(2',4',6'-Trimethylphenyl)]hydroxymethylimidazole

The procedure of Example 1 is repeated, except that bromomesitylene is used. After recrystallization from water-ethanol, the product melts at 186°–188° C.

NMR: 1.95 (s, 9H), 4.6 (s, 2H), 5.95 (s, 1H), 6.3 (s, 1H), 6.5 (s, 2H), 7.25 (s, 1H).

EXAMPLE 15

5-Methyl-4-[α-(2',6'-dimethylphenyl)]hydroxymethylimidazole

The procedure of Example 1 is repeated, except that 1-bromo-2,6-dimethylbenzene is used in place of 2-bromotoluene and 5-methyl-4-imidazolealdehyde is used in place of 4-imidazolealdehyde. The melting point of the free base, after recrystallization from $H_2O$-ethanol, is 277°–278° C. The melting point of the hydrochloride is >300° C.

NMR: (HCl salt) 1.7 (s, 3H), 2.2 (s, 6H), 4.75 (s, 3H), 6.4 (s, 1H), 7.1 (s, 3H), 8.65 (s, 1H).

EXAMPLE 16

5-Methyl-4-(α-phenyl)hydroxymethylimidazole

The procedure of Example 15 is repeated, except that bromobenzene is used in place of 1-bromo-2,6-dimethylbenzene. After recrystallization from water-ethanol, the product melts at 140°–143° C.

NMR: 1.75 (s, 3H), 4.9 (s, 2H), 5.55 (s, 1H), 7.0 (m, 6H).

EXAMPLE 17

4-(2'-Methylbenzyl)imidazole 5.9 g of 4-[α-(2'-methylphenyl)]hydroxymethylimidazole are dissolved in 40 ml of 4 N HCl solution. About 60 mg of 10% palladium-on-carbon (Pd/C) are added and the mixture is stirred vigorously under a hydrogen atmosphere at about 60° C. until no more hydrogen is consumed (about 4 hours). The reaction mixture is then filtered and washed twice with 10 ml portions of chloroform. The aqueous phase is then made alkaline (pH about 9) with sodium hydroxide solution and extracted with chloroform (3×10 ml). The combined chloroform extracts are washed with water (1×10 ml), dried over $Na_2SO_4$ and evaporated to dryness. The crude product is purified by converting it into the hydrochloride in acetone. The melting point of the hydrochloride is 133°–135° C.

NMR (HCl salt): 2.1 (s, 3H), 3.85 (s, 2H), 4.75 (s, 2H), 6.9 (s, 1H), 7.1 (s, 4H), 8.5 (s, 1H).

MS: 172 (100%), 171 (40%), 157 (30%), 144 (21%), 130 (17%), 128 (14%), 115 (13%), 104 (33%), 81 (17%).

EXAMPLE 18

4-(2′,6′-Dimethylbenzyl)imidazole 10 g of 4-[α-(2′,6′-dimethylphenyl)]hydroxymethyl-1H-imidazole are dissolved in 100 ml of acetic acid. 100 mg of 10% Pd/C are added and the reaction mixture is stirred vigorously in a hydrogen atmosphere at about 60° C. until the reaction is completed. The mixture is then filtered and distilled to a smaller volume. 70 ml of water are added and that mixture is then washed twice with 20 ml portions of chloroform. The aqueous phase is made alkaline with sodium hydroxide solution and extracted with chloroform (3×40 ml). The combined chloroform extracts are washed with water (1×10 ml) and dried over Na$_2$SO$_4$. The solution is evaporated to dryness. The crude product is crystallized from ethyl acetate to give a product melting at 126°–128° C. The corresponding hydrochloride, prepared in ethyl acetate, melts at 207°–210° C.

NMR (HCl salt): 1.95 (s, 6H), 3.8 (s, 2H), 4.65 (s, 2H), 6.55 (s, 1H), 6.8 (s, 3H), 8.55 (s, 1H).

MS: 186 (100%), 185 (37%), 171 (41%), 158 (12%), 144 (15%), 143 (11%), 142 (18%), 118 (42%), 91 (11%), 81 (21%).

EXAMPLE 19

4-(3′-Methylbenzyl)imidazole

The procedure of Example 17 is repeated, except that 4-[60-(3′-methylphenyl)]hydroxymethylimidazole is used in place of 4-[α-(2′-methylphenyl)]hydroxymethyimidazole. The corresponding hydrochloride is then prepared in ethyl acetate, m.p. 127°–130° C.

NMR (HCl salt): 2.25 (s, 3H), 3.95 (s, 2H), 4.65 (s, 2H), 7.15 (m, 5H), 8.55 (s, 1H).

EXAMPLE 20

4-(4′-Methylbenzyl)imidazole

The procedure of Example 18 is repeated, except that 4-[α-(4′-methylphenyl)]hydroxymethylimidazole is used in place of 4-[α-(2′,6′-dimethylphenyl)]hydroxymethylimidazole. The hydrochloride salt melts at 161°–164° C.

NMR (HCl salt): 2.1 (s, 3H), 3.8 (s, 2H), 4.8 (s, 2H), 7.0 (s, 5H), 8.45 (s, 1H).

EXAMPLE 21

4-(2′,4′-Dimethylbenzyl)imidazole

The procedure of Example 17 is repeated, except that 4-[α-(2′,4′-dimethylphenyl)]hydroxymethylimidazole is used. After recrystallization from ethylacetate-isopropanol, the corresponding hydrochloride is prepared in ethyl acetate. It melts at 151°–153° C.

NMR (HCl salt): 2.25 (s, 6H), 4.05 (s, 2H), 4.9 (s, 2H), 7.0 (s, 3H), 7.15 (s, 1H), 8.85 (s, 1H).

EXAMPLE 22

4-(2′,3′-Dimethylbenzyl)imidazole

The procedure of Example 17 is repeated, except that 4-[α-(2′,3′-dimethylphenyl)]hydroxymethylimidazole is used. The product, after recrystallization from acetone, melts at 114°–116° C.

NMR: 1.6 (s, 3H), 1.65 (s, 3H), 3.35 (s, 2H), 4.1 (s, 1H), 6.0 (s, 1H), 6.4 (m, 3H), 7.0 (s, 1H).

EXAMPLE 23

4-(3′,4′-Dimethylbenzyl)imidazole

The procedure of Example 17 is repeated, except that 4[α-(3′,4′-dimethylphenyl)]hydroxymethylimidazole is used. The melting point of the hydrochloride is 158°–163° C.

NMR (HCl salt): 1.95 (s, 6H), 3.75 (s, 2H), 4.65 (s, 2H), 6.85 (s, 3H), 6.95 (s, 1H), 8.45 (s, 1H).

EXAMPLE 24

4-(2′-Ethylbenzyl)imidazole

The procedure of Example 17 is repeated, except that 4-[α-(2′-ethylphenyl)]hydroxymethylimidazole is used. The product, after recrystallization from n-butylacetate, melts at 104°–106° C.

NMR (HCl salt): 1.3 (t, 3H), 2.83 (q, 2H), 4.3 (s, 2H), 5.5 (s, 2H), 7.35 (s, 5H), 9.05 (s, 1H).

EXAMPLE 25

4-(2′,4′,6′-Trimethylbenzyl)imidazole

The procedure of Example 17 is repeated, except that 4-(2′,4′,6′-trimethylphenyl)hydroxymethylimidazole is used. The melting point of the hydrochloride is 167°–170° C.

NMR (HCl salt): 1.95 (s, 9H), 3.85 (s, 2H), 4.85 (s, 2H), 6.45 (s, 1H), 6.65 (s, 2H), 8.6 (s, 1H).

EXAMPLE 26

4-(2′-Methoxybenzyl)imidazole

The procedure of Example 17 is repeated, except that 4-[α-(2′-methoxyphenyl)]hydroxymethylimidazole is used.

NMR (HCl salt): 3.55 (s, 3H), 3.65 (s, 2H), 4.65 (s, 1H), 6.8 (s, 5H), 8.3 (s, 1H).

EXAMPLE 27

4-(3′-Methoxybenzyl)imidazole

The procedure of Example 17 is repeated, except that 4-[α-(3′-methoxyphenyl)]hydroxymethylimidazole is used. The melting point of the hydrochloride is 151°–153° C.

NMR (HCl salt): 3.55 (s, 3H), 3.75 (s, 2H), 4.6 (m, 2H), 6.65 (m, 3H), 6.95 (s, 1H), 7.1 (s, 1H), 8.4 (s, 1H).

EXAMPLE 28

4-(4′-Methoxybenzyl)imidazole

The procedure of Example 17 is repeated, except that 4-[α-(4′-methoxyphenyl)]hydroxymethylimidazole is used.

NMR: 3.5 (s, 3H), 3.75 (s, 2H), 6.85 (m, 5H), 7.3 (s, 1H), 12.2 (s, 1H).

EXAMPLE 29

4-(α-Phenyl)ethoxymethyimidazole 10 g of 4-(α-phenyl)hydroxymethylimidazole are dissolved in 60 ml of absolute ethanol. Hydrogen chloride gas is passed into the solution for 1 hour, during which time the reaction mixture is maintained at reflux, with stirring. The mixture is then evaporated to dryness. 60 ml of water are added to dissolve the distillation residue, then the solution is made alkaline with sodium carbonate and extracted three times with 50 ml portions of chloroform. The combined chloroform extracts are washed with water and dried over sodium sulfate. The filtrate is evaporated to dryness to give a crude product, which after recrystallization from ethyl acetate melts at 129°–131° C.

NMR: 0.85 (t, 3H), 3.5 (q, 2H), 4.9 (s, 1H), 5.1 (s, 1H), 6.45 (s, 1H), 7.0 (s, 5H), 7.25 (s, 1H).

EXAMPLE 30

4-[α-(2'-Methylphenyl)]ethoxymethylimidazole

The procedure of Example 29 is repeated, except that 4-[α-(2'-methylphenyl)]hydroxymethylimidazole is used in place of 4-(α-phenyl)hydroxymethylimidazole.

NMR: 1.0 (t, 3H), 2.1 (s, 2H), 3.45 (q, 2H), 4.4 (s, 2H), 5.65 (s, 1H), 7.1 (m, 5H), 9.15 (s, 1H).

EXAMPLE 31

4-[α-(2',6'-Dimethylphenyl)]ethoxymethyl-5-methylimidazole

The procedure of Example 29 is repeated, except that 4-[α-(2',6'-dimethylphenyl)]hydroxymethyl-5-methylimidazole is used.

NMR (HCl salt): 1.05 (1, 3H), 1.65 (s, 3H), 2.1 (s, 6H), 3.4 (q, 2H), 4.65 (s, 2H), 5.95 (s, 1H), 6.95 (s, 3H), 8.5 (s, 1H).

MS: 244 (38%), 229 (9%), 215 (15%), 199 (39%), 183 (100%), 162 (39%), 139 (29%), 133 (35%), 111 (25%), 109 (17%), 105 (13%).

EXAMPLE 32

4-[α-(2',6'-Dimethylphenyl)]ethoxymethylimidazole

The procedure of Example 29 is repeated, except that 4-[α-(2',6'-dimethylphenyl)]hydroxymethylimidazole is used. The product melts at 142°–147° C. The corresponding hydrochloride, prepared in a mixture of ethyl acetate and isopropanol, melts at 136°–139° C.

NMR (HCl salt): 1.1 (t, 3H), 2.15 (s, 6H), 3.4 (q, 2H), 4.6 (s, 2H), 6.0 (s, 1H), 6.85 (s, 1H), 7.05 (m, 3H), 8.65 (s, 1H).

EXAMPLE 33

4-[α-(3'-Methylphenyl)]ethoxymethylimidazole

The procedure of Example 29 is repeated, except that 4-[α-(3'-methylphenyl)]hydroxymethylimidazole is used. The hydrochloride, prepared in isopropanol-ethyl acetate, melts at 135°–140° C.

NMR (HCl salt): 1.2 (t, 3H), 2.25 (s, 3H), 3.55 (q, 2H), 4.75 (s, 2H), 5.55 (s, 1H), 7.1 (s, 1H), 8.7 (s, 1H).

MS: 216 (23%), 187 (6%), 172 (53%), 171 (100%), 170 (20%), 155 (7%), 144 (15%), 143 (27%), 97 (20%), 95 (23%), 91 (15%).

EXAMPLE 34

4-[α-3'-Methoxyphenyl)]ethoxymethylimidazole

The procedure of Example 29 is repeated, except that 4-[α-(3'-methoxyphenyl)]hydroxymethylimidazole is used.

NMR (HCl salt): 1.05 (t, 3H), 3.4 (q, 2H), 3.6 (s, 3H), 4.75 (s, 2H), 5.45 (s, 1H), 6.9 (m, 5H), 8.65 (s, 1H).

EXAMPLE 35

4-[α-(4'-Methoxyphenyl)]ethoxymethylimidazole

The procedure of Example 29 is repeated, except that 4-[α-(4'-methoxyphenyl)]hydroxymethylimidazole is used.

NMR (HCl salt): 1.0 (t, 3H), 3.3 (q, 2H), 3.55 (s, 3H), 4.7 (s, 2H), 5.4 (s, 1H), 6.95 (m, 5H), 8.6 (s, 1H).

EXAMPLE 36

4-[α-(2',6'-Dimethylphenyl)]methoxymethylimidazole 10 g of 4-[α-(2',6'-dimethylphenyl)]hydroxymethylimidazole is dissolved in 60 ml of methanol. Hydrogen chloride gas is passed into the solution for 1 hour, during which time the mixture is maintained at reflux. The mixture is then evaporated to dryness. 100 ml of water are added and the solution is made alkaline with sodium carbonate. The solution is then extracted three times with 50 ml portions of chloroform. The combined chloroform extracts are washed with water, dried over sodium sulfate and filtered, and the filtrate is evaporated to dryness. The corresponding hydrochloride, prepared in ethyl acetate-isopropanol, melts at 176°–179° C.

NMR (HCl salt): 2.2 (s, 6H), 3.3 (s, 3H), 4.7 (s, 2H), 6.0 (s, 1H), 6.9 (s, 1H), 7.15 (s, 3H), 8.7 (s, 1H).

EXAMPLE 37

5-Methyl-4-(2',6'-dimethylbenzyl)imidazole 6 g of 5-methyl-4-[α-(2',6'-dimethylphenyl)]-ethoxymethylimidazole are dissolved in 50 ml of acetic acid. About 60 mg of 10% palladium-on-carbon are added and the mixture is stirred vigorously in hydrogen atmosphere at about 60° C. for as long as hydrogen is consumed (about 6 hours). The mixture is then cooled and filtered. The filtrate is distilled to a smaller volume and 50 ml of water are added. The resultant solution is made alkaline with sodium hydroxide solution, with cooling. The precipitate which forms is filtered and washed with water. The product melts at 142°–145° C.

NMR: 1.5 (s, 3H), 1.85 (s, 6H), 3.6 (s, 2H), 4.1 (s, 1H), 6.7 (s, 3H), 7.0 (s, 1H).

MS: 200 (99%), 199 (12%), 185 (44%), 172 (6%), 118 (100%), 95 (19%).

EXAMPLE 38

5-Methyl-4-(2'-methylbenzoyl)imidazole 4.9 g of dry magnesium turnings are covered with 50 ml of dry tetrahydrofuran. The mixture is heated to boiling and a solution of 34 g of 2-bromotoluene in 50 ml of dry tetrahydrofuran is added dropwise at such a rate that a smooth reaction is maintained. After the addition is complete, the reaction mixture is refluxed for about 30 minutes until the magnesium turnings no longer react. The reaction mixture is then cooled to about 50° C. and 20 g of 5-methyl-4-imidazole-carboxylic acid methyl ester are added in small portions. After the addition is complete, the mixture is refluxed for another 2 hours and the solvent is then distilled off to give about half of the original volume. The mixture is cooled and poured into 300 ml of cold water containing 15 ml of concentrated sulfuric acid, with agitation. The stirring is continued for an additional 15 minutes and the mixture is then filtered. The pH of the filtrate is adjusted to 7–11 and the solution is extracted three times with 30 ml portions of chloroform. The combined chloroform extracts are washed with water and evaporated to dryness. The residue, which contains the crude product, is converted to the hydrochloride in ethanol. After recrystallization from ethanol, the hydrochloride melts at 289°–291° C. The 5-methyl-4-(2'-methylbenzoyl)-1H-imidazole is liberated from the hydrochloride in water with sodium hydroxide. It melts at 165°–166° C.

NMR (HCl salt): 2.0 (s, 3H), 2.15 (s, 3H), 4.75 (s, 2H), 7.3 (s, 4H), 8.8 (s, 1H).

MS: 200 (33%), 185 (100%), 172 (15%), 171 (14%), 119 (14%), 110 (11%), 91 (25%).

EXAMPLE 39

5-Methyl-4-(2',6'-dimethylbenzoyl)imidazole

The procedure of Example 38 is repeated, except that 1-bromo-2,6-dimethylbenzene is used in place of 2-bromotoluene. The melting point of the hydrochloride is 268°–271° C. The base, which is liberated from the hydrochloride in water, has a melting point of 179°–181° C.

NMR (HCl salt): 1.9 (s, 3H), 2.01 (s, 3H), 2.07 (s, 3H), 4.7 (s, 2H), 7.15 (m, 3H), 8.9 (s, 1H).

EXAMPLE 40

5-Methyl-4-[α-(2'-methylphenyl)]hydroxymethylimidazole

B 5.1 g of 5-methyl-4-(2'-methylbenzoyl)imidazole are dissolved in 25 ml of ethanol. 0.9 g of sodium borohydride is added while stirring at room temperature. After the addition is complete, the mixture is stirred for 4 hours at room temperature, then is evaporated to dryness. 30 ml of water are added to the residue and the resultant mixture is stirred and cooled. The precipitate is removed by filtration and washed with water. After recrystallization from water-ethanol, the product melts at 148°–150° C.

NMR: 1.65 (s, 3H), 1.8 (s, 3H), 4.7 (s, 2H), 5.65 (s, 1H), 7.0 (m, 4H), 7.1 (s, 1H).

MS: 202 (75%), 185 (24%), 184 (68%), 183 (35%), 168 (100%), 157 (16%), 156 (13%), 120 (11%), 119 (15%), 115(19%), 111(b48%), 109(27%), 91(26%), 89 (55%).

EXAMPLE 41

5-Methyl-4-(2'-methylbenzyl)imidazole 2.1 g of 5-methyl-4-(2'-methylbenzoyl)imidazole are dissolved in 10 ml of acetic acid. 0.2 g of 10% palladium-on-carbon is added and the reaction mixture is agitated vigorously at about 60° C. in a hydrogen atmosphere until the uptake of hydrogen ceases. The mixture is then cooled and filtered and the filtrate is evaporated to dryness. The residue is dissolved in 20 ml of water and the resultant solution is made alkaline (pH about 10) with sodium hydroxide. The precipitate which forms is removed by filtration, washed with water and dried. The product is transformed to the hydrochloride in isopropanol, its melting point after recrystallization from water-ethanol being 226°–268° C. The free base, 5-methyl-4-(2'-methylbenzyl)imidazole, which is liberated from the hydrochloride in water with sodium hydroxide, has a melting point of 138°–140° C.

NMR (HCl salt): 1.95 (s, 3H), 2.05 (s, 3H), 3.7 (s, 2H), 4.6 (s, 2H), 7.05 (s, 4H), 8.35 (d, 1H).

MS: 186 (100%), 185 (26%), 158 (7%), 144 (9%), 115 (8%), 104 (53%), 95 (18%).

EXAMPLE 42

4-(2'-Methylbenzoyl)imidazole 5.0 g of 4-[α-(2'-methylphenyl)]hydroxymethylimidazole are added in small portions to 12.5 ml of 65% nitric acid heated to 60° C. The mixture is stirred at about 80° C. for 5 hours, then is distilled to a smaller volume. 50 ml of water are added and the resultant solution is made alkaline with sodium hydroxide (ph about 12) with cooling. The alkaline solution is filtered and the filtrate is neutralized with diluted hydrochloric acid (pH =7), cooled and filtered. The precipitate is washed with water and dried to yield crude 4-(2'-methylbenzoyl)imidazole.

EXAMPLE 43

4-(2',6'-Dimethylbenzoyl)imidazole

The procedure of Example 42 is repeated, except that the imidazole starting material is 4-[α-(2',6'-dimethylphenyl)]hydroxymethylimidazole. The product melts at 131°–133° C.

NMR: 1.75 (s, 6H), 4.8 (s, 1H), 6.7 (m, 3H), 7.0 (s, 1H), 7.55 (s, 1H).

EXAMPLE 44

4-(4'-Methylbenzoyl)imidazole

The procedure of Example 42 is repeated, except that the imidazole starting material is 4-[α-(4-methylphenyl)-]hydroxymethylimidazole. The hydrochloride, which is prepared in isopropanol, melts at 205°–210° C.

NMR: 2.55 (s, 3H), 4.85 (s, 2H), 7.85 (m, 4H), 8.35 (s, 1H), 9.20 (s, 1H).

MS: 186 (100%), 171 (37%), 159 (33%), 119 (87%), 95 (48%), 91 (52%).

EXAMPLE 45

4-(2',6'-Dimethyl-3'-nitrobenzoyl)imidazole 10 g of 4-[α-(2',6'-dimethylphenyl)]hydroxymethylimidazole are dissolved in 30 ml of concentrated nitric acid and the solution is heated with stirring at 100° C. for 10 hours. 150 ml of water are then added and the solution is evaporated to a smaller volume in order to remove the excess of nitric acid. Water is added and the reaction mixture is neutralized with sodium hydroxide, with cooling. The precipitate which forms is filtered and worked with water and ethanol. The product melts at 210°–215° C. The corresponding hydrochloride, prepared in isopropanol, melts at 245°–249° C.

NMR: 2.4 (s, 6H), 5.15 (s, 2H), 7.85 (m, 2H), 8.25 (s, 1H), 9.45 (s, 1H).

MS: 245 (100%), 244 (7%), 230 (8%), 228 (18%), 217 (65%). 200 (15%), 199 (11%), 198 (18%), 171 (19%), 95 (71%).

EXAMPLE 46

4-(4'-Amino-3',5'-dichlorobenzyl)-5-methylimidazole

A mixture of 6.0 g of 4-chloromethyl-5-methylimidazole hydrochloride, 9.0 g of 2,6-dichloroaniline and 40 ml of xylene is refluxed with stirring for 3 hours. The mixture is then filtered and the precipitate is washed with xylene. The precipitate is dissolved in 50 ml of water and the pH is adjusted to 8. The solution is extracted with toluene (3×30 ml). The combined toluene extracts are washed with 10 ml of water and evaporated to dryness. The residue, which is crude 4-(4'-amino-3',5'-dichlorobenzyl)-5- methylimidazole, is converted to the hydrochloride in isopropanol with HCl-ethyl acetate. The free base is liberated from the hydrochloride in water with sodium hydroxide. The melting point of the base is 172°–175° C.

NMR: (HCl salt): 2.0 (s, 3H), 4.5 (s, 2H), 4.8 (s, 4H), 7.25 (s, 2H), 8.55 (s, 1H).

MS: 254 (2%), 220 (15%), 189 (6%), 164 (8%), 163 (43%), 162 (5%), 161 (67%), 95 (100%).

EXAMPLE 47

4-(4'-Amino-3',5'-dichlorobenzyl)imidazole

The procedure of Example 46 is repeated, except that 4-chloromethylimidazole is used in place of 4-chloromethyl-5-methylimidazole. The product melts at 178°–181° C.

EXAMPLE 48

4-(2',4',6'-Trimethylbenzyl)imidazole 3.0 g of 4-chloromethylimidazole hydrochloride are suspended in 20 ml of mesitylene. 5 ml of dimethylformamide are added and the reaction mixture is refluxed for 12 hours, then cooled. 30 ml of water are added, the layers are separated, and the aqueous phase is washed with chloroform. The aqueous solution is then made alkaline with sodium carbonate solution and extracted with chloroform. The combined chloroform extracts are washed with water and evaporated to dryness. The residue, which is crude 4-(2',4',6'-trimethylbenzyl)imidazole, is converted to the hydrochloride by treatment with concentrated hydrochloric acid. The hydrochloride salt melts at 166°–169° C.

EXAMPLE 49

(a) 2,6-Dichlorobenzylglyoxal diethyl acetal 2.4 g of magnesium turnings are covered with 100 ml of dry diethyl ether. To that mixture is then added dropwise a solution of 24 g of 2,6-dichlorobenzylbromide in 50 ml of dry diethyl ether at such a rate that a smooth reaction is maintained. After the addition is complete, the reaction mixture is refluxed for one additional hour, then is cooled to room temperature. The reaction mixture is then added dropwise, over a period of 2 hours, to a cooled (0°–5° C.) solution of diethyoxyacetic acid piperidinyl amide (21.5 g) in 100 ml of diethyl ether. After the addition is complete, the reaction mixture is stirred for an additional hour at 5° C. The mixture is then poured into cold sulfuric acid (400 ml of water containing 30 ml of concentrated sulfuric acid). The ether layer is separated and evaporated to dryness. The residue, which consists of crude 2,6-dichlorobenzylglyoxal diethylacetal, is distilled under reduced pressure (130°–140° C./1 mmHg) and used in Example 49(b) and 50(a) set forth below.

(b) 1,1-Diethoxy-2-hydroxy-3-(2',6'-dichlorophenyl)propane 29.1 g of 2,6-dichlorobenzylglyoxal diethylacetal are dissolved in 200 ml of ethanol and to the solution is then added, in small portions at room temperature, 1.9 g of sodium borohydride. After the addition is complete, the mixture is stirred at room temperature for another four hours. 200 ml of water are added and the solution is extracted with ethyl acetate. The combined ethyl acetate extracts are washed with water and evaporated to dryness. The residue, which consists of crude 1,1-diethoxy-2-hydroxy-3-(2',6'-dichlorophenyl)propane, is used in steps (c) and (e) of this Example as set forth below.

(c) 1-(2',6'-Dichlorophenyl)-3-hydroxy-2-propanone 10 g of 1,1-diethoxy-2-hydroxy-3-(2',6'-dichlorophenyl)propane are dissolved in 40 ml of ethanol, 20 ml of concentrated hydrochloric acid are added, and the mixture is refluxed for 4 hours, then is evaporated to dryness. 10 ml of toluene are added and the solution is again evaporated to dryness in order to remove the water. The residue, crude 1-(2',6'-dichlorophenyl)-3-hydroxy-2-propanone, is used in Example 49 (d) below. After recrystallization from diisopropyl ether, the product melts at 111°–114° C.

(d) 4-(2',6'-Dichlorobenzyl)imidazole 9.0 g of 1-(2',6'-dichlorophenyl)-3-hydroxy-2-propanone and 20 ml of formamide are combined. The mixture is heated at 180° C. for 4 hours, then is cooled and diluted with 50 ml of water. The pH is adjusted with hydrochloric acid to 3–4 and the reaction mixture is washed three times with 50 ml portions of chloroform. The aqueous layer is then made alkaline with sodium hydroxide (pH=8–9) and the mixture is extracted three times with 50 ml portions of chloroform. The combined chloroform extracts are washed with water, and evaporated to dryness. The residue, which consists of the crude product, is converted to the hydrochloride in ethyl acetate-isopropol. The hydrochloride melts at 244°–248° C. The base, which is liberated from the hydrochloride in water with sodium hydroxide, melts at 142°–145° C.

NMR (HCl salt): 4.15 (s, 2H), 4.65 (s, 2H), 7.0 (s, 1H), 7.2 (m, 3H), 8.55 (s, 1H).

MS: 228 (10%), 226 (16%), 193 (30%), 192 (13%), 191 (100%), 166 (12%), 164 (37%), 156 (15%), 81 (15%).

(e) 4-(2',6'-Dichlorobenzyl)imidazole 5.0 g of 1,1-diethoxy-2-hydroxy-3-(2',6'-dichlorophenyl)propane and 15 ml of formamide are combined and the mixture is heated with stirring at 180° C. for 4 hours. Excess formamide is removed by distillation and the reaction mixture is diluted with water. The pH is adjusted with hydrochloric acid to 3–4. Subsequent treatment is described in (d) above. The hydrochloride melts at 244°–248° C.

EXAMPLE 50

(a) 2,6-Dichlorobenzylglyoxal

A mixture of 10 g of 2,6-dichlorobenzylglyoxal diethylacetal, 40 ml of ethanol and 20 ml of concentrated hydrochloric acid is refluxed for 4 hours and then is evaporated to dryness. The residue, which is a yellowish oil, consists of crude 2,6-dichlorobenzylglyoxal and is used in step (b) of this Example as set forth below.

(b) 4-(2',6'-Dichlorobenzyl)oxazole 21.7 g of crude 2,6-dichlorobenzylglyoxal are dissolved in 50 ml of formamide. 7.0 g of hexamethylenetetramine and 30.8 g of ammonium acetate are added and the reaction mixture is stirred at 100° C. for 2 hours, then is evaporated to dryness in vacuo. 200 ml of water are added and the pH of the aqueous phase is adjusted, while stirring, to 2–3 with concentrate hydrochloric acid. The solution is washed with toluene (3×50 ml). The aqueous solution is made alkaline with sodium hydroxide (pH=8-9) and then extracted three times with chloroform (1×100 ml and 2×50 ml). The combined chloroform extracts are washed with water, dried with sodium sulfate and evaporated to dryness. The residue, which consisted of crude product, is used in step (c) below.

(c) 4-(2',6'-Dichlorobenzyl)imidazole

A mixture of 10 g of 4-(2',6'-dichlorobenzyl)oxazole and 30 ml of formamide is stirred at 180° C. for 4 hours. The mixture is cooled and diluted with water. The reaction product is thereafter isolated in the same manner as described in Example 49(d).

EXAMPLE 51

4-(2'-Chlorobenzyl)imidazole

The procedure of Example 49(e) is repeated except that 1,1-diethoxy-2-hydroxy-3-(2'-chlorophenyl)propane is used in place of the 1,1-diethoxy-2-hydroxy-3-(2',6'-dichlorophenyl)propane. The product melts at 168°-171° C.

NMR (HCl salt): 4.05 (s, 2H), 4.65 (s, 2H), 7.05 (s, 1H), 7.25 (s, 4H), 8.55 (s, 1H).

EXAMPLE 52

4-(2'-Methylbenzyl)imidazole

A mixture of 1.7 g of 1-(2'-methylphenyl)-3-chloro-2,3-epoxypropane and 10 ml of formamide is refluxed for 22 hours. Excess formamide is distilled off and 20 ml of water are added. The mixture is extracted with chloroform (3×10 ml) and the aqueous phase is made alkaline with sodium hydroxide. The alkaline solution is then extracted three times with 10 ml portions of chloroform and the combined chloroform extracts are washed with water, dried with sodium sulfate and evaporated to dryness. The residue, which is crude 4-(2'-methylbenzyl)imidazole, is transformed to the hydrochloride in acetone by adding an ethyl acetate solution containing dry hydrogen chloride. The melting point of the hydrochloride is 131°-134° C.

NMR (HCl salt): 2.1 (s, 3H), 3.85 (s, 2H), 4.75 (s, 2H), 6.9 (s, 1H), 7.1 (s, 4H), 8.5 (s, 1H).

EXAMPLE 53

4-(2',3'-Dimethylbenzyl)imidazole

A mixture of 7.6 g of 4-(2',3'-dimethylbenzyl)-N-acetylimidazole and 30 ml of 6 N hydrochloric acid is refluxed with stirring for 4 hours. The mixture is distilled to a smaller volume and 50 ml of water are added. The pH is adjusted with sodium hydroxide to 8-9. The mixture is cooled and filtered and the filter cake is washed with water and dried. The product melts at 110°-115° C.

NMR: 1.6 (s, 3H), 1.65 (s, 3H), 3.35 (s, 2H), 4.1 (s, 1H), 6.0 (s, 1H), 6.4 (m, 3H), 7.0 (s, 1H).

EXAMPLE 54

4-(2'-Methylbenzyl)imidazole 10 g of 4-[α-(2'-methylphenyl)]chloromethylimidazole is dissolved in 50 ml of ethanol. 0.1 g of 10% palladium-on-carbon is added and the reaction mixture is stirred at room temperature in a hydrogen atmosphere until no more hydrogen is consumed. The mixture is then filtered and the filtrate is evaporated to dryness. 50 ml of water are added to the residue and the resulting solution is made alkaline (pH=8-9) with sodium hydroxide. The solution is extracted with chloroform, and the chloroform extracts are washed with water and evaporated to dryness. The residue is dissolved in acetone. HCl and ethyl acetate are added, thus affording the hydrochloride, melting at 132°-133° C.

EXAMPLE 55

4-(2'-Methylbenzyl)imidazole 12.3 g of N-benzyl-4-(2'-methylbenzyl)imidazole are dissolved in 100 ml of ethanol. 0.3 g of 10% palladium-on-carbon is added and the reaction mixture is stirred vigorously at 70° C. in a hydrogen atmosphere until the uptake of hydrogen ceases. The mixture is cooled and filtered. Subsequent treatment as described in Example 54 above affords the desired product.

EXAMPLE 56

4-(3',5'-Dimethyl-4'-hydroxybenzyl)imidazole

To a solution of 12.2 g of 2,6-dimethylphenol in methanol are added 20 ml of 30% sodium methoxide solution, and the resultant mixture is warmed to 50° C. The mixture is maintained at that temperature while 5.8 g of 4-chloromethylimidazole in methanol are added, with stirring. After the addition is complete, the reaction mixture is stirred at 50°-60° C. for about 4 hours, then is cooled and poured into cold water. That mixture is acidified with hydrochloric acid and washed with ethyl acetate. The pH of the aqueous solution is then adjusted to 7-8, and the product is obtained by extraction with ethyl acetate. The desired 4-(3',5'-dimethyl-4'-hydroxybenzyl)imidazole is obtained in 54% yield. The free base is converted to the corresponding hydrochloride salt by treatment with HCl in a mixture of ethyl acetate and isopropanol. That salt melts at 210°-214° C.

NMR (HCl salt): 2.31 (s, 6H), 3.97 (s, 2H), 4.91 (s, 3H), 6.99 (s, 2H), 7.27 (s, 1H), 8.70 (s, 1H).

13C-NMR (HCl salt): 18.345 (q), 31.816 (t), 118.244 (d), 128.173 (s), 131.261 (s), 131.261 (d), 135.620 (d), 136.165 (s), 153.390 (s).

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims.

What we claim is:

1. A compound of the formula:

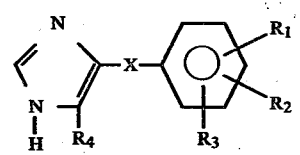

wherein $R_1$, $R_2$ and $R_3$, which can be the same or different, are each hydrogen, chloro, bromo, fluoro, methyl, ethyl, methoxy, amino, hydroxy or nitro; $R_4$ is hydrogen or alkyl of 1 to 7 carbon atoms; —X— is

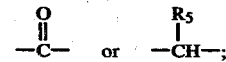

$R_5$ is hydrogen, hydroxy or —$OR_6$; and $R_6$ is alkyl of 1 to 7 carbon atoms or aryl of 6 to 10 carbon atoms; or a non-toxic pharmaceutically acceptable acid addition salt thereof; with the provisos that:

(a) when $R_1$, $R_2$ and $R_3$ are simultaneously hydrogen, then —X— is other than

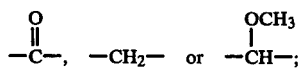

and (b) when $R_1$ is 2-methyl, $R_2$ is 5-methyl, $R_3$ is hydrogen and $R_4$ is methyl, then —X— is other than —$CH_2$—.

2. A compound of claim 1 wherein —X— is

3. A compound of claim 1 wherein —X— is —$CH_2$—.

4. A compound of claim 1 wherein —X— is

5. A compound of claim 1 wherein —X— is

6. A compound of claim 5 wherein $R_6$ is $CH_3$.

7. A compound of claim 5 wherein $R_6$ is $C_2H_5$.

8. A compound of claim 2, 3, 4, 5, 6 or 7 wherein $R_4$ is hydrogen.

9. A compound of claim 2, 3, 4, 5, 6 or 7 wherein $R_4$ is methyl.

10. A compound of claim 2 wherein $R_1$, $R_2$ and $R_3$, which can be the same or different, are each hydrogen, chloro, bromo, fluoro, methyl, ethyl, hydroxy or methoxy.

11. A compound of claim 10 wherein $R_4$ is hydrogen or methyl.

12. A compound of claim 3 wherein $R_1$, $R_2$ and $R_3$, which can be the same or different, are each hydrogen, chloro, bromo, fluoro, methyl, ethyl, hydroxy or methoxy.

13. A compound of claim 12 wherein $R_4$ is hydrogen or methyl.

14. A compound of claim 4 wherein $R_1$, $R_2$ and $R_3$, which can be the same or different, are each hydrogen, chloro, bromo, fluoro, methyl, ethyl, hydroxy or methoxy.

15. A compound of claim 14 wherein $R_4$ is hydrogen or methyl.

16. A compound of claim 5 wherein $R_1$, $R_2$ and $R_3$, which can be the same or different, are each hydrogen, chloro, bromo, fluoro, methyl, ethyl, hydroxy or methoxy.

17. A compound of claim 16 wherein $R_4$ is hydrogen or methyl.

18. A compound of claim 6 wherein $R_1$, $R_2$ and $R_3$, which can be the same or different, are each hydrogen, chloro, bromo, fluoro, methyl, ethyl, hydroxy or methoxy.

19. A compound of claim 18 wherein $R_4$ is hydrogen or methyl.

20. A compound of claim 7 wherein $R_1$, $R_2$ and $R_3$, which can be the same or different, are each hydrogen, chloro, bromo, fluoro, methyl, ethyl, hydroxy or methoxy.

21. A compound of claim 20 wherein $R_4$ is hydrogen or methyl.

22. A compound of claim 1, 10, 11, 12, 13, 14, 15, 16, 17, 18, 19, 20 or 21 wherein at least one of $R_1$, $R_2$ and $R_3$ is other than hydrogen.

23. A compound of claim 1, 10, 11, 12, 13, 14, 15, 16, 17, 18, 19, 20 or 21 wherein $R_2$ and $R_3$ are hydrogen and $R_1$ is a substituent in the 2-, 3- or 4-position selected from the group consisting of chloro, bromo, fluoro, methyl, ethyl, hydroxy and methoxy.

24. A compound of claim 23 wherein $R_1$ is methyl, ethyl, methoxy or chloro.

25. A compound of claim 1, 10, 11, 12, 13, 14, 15, 16, 17, 18, 19, 20 or 21 wherein $R_3$ is hydrogen and $R_1$ and $R_2$ are substituents in the 2,3-, 2,4- or 2,6-positions selected from the group consisting of chloro, bromo, fluoro, methyl, ethyl, hydroxy and methoxy.

26. A compound of claim 25 wherein $R_1$ and $R_2$ are identical.

27. A compound of claim 26 wherein $R_1$ and $R_2$ are each methyl, ethyl, methoxy or chloro.

28. A compound of claim 1, 10, 11, 12, 13, 14, 15, 16, 17, 18, 19, 20 or 21 wherein $R_1$, $R_2$ and $R_3$ are substituents in the 2,4,6-positions selected from the group consisting of chloro, bromo, fluoro, methyl, ethyl, hydroxy and methoxy.

29. A compound of claim 28 wherein $R_1$, $R_2$ and $R_3$ are identical.

30. A compound of claim 29 wherein $R_1$, $R_2$ and $R_3$ are each methyl, ethyl, methoxy or chloro.

31. A compound of claim 1 which is selected from the group consisting of 4-(2'-methylbenzyl)imidazole and its non-toxic pharmaceutically acceptable acid addition salts.

32. A compound of claim 1 which is selected from the group consisting of 4-(3'-methylbenzyl)imidazole and its non-toxic pharmaceutically acceptable acid addition salts.

33. A compound of claim 1 which is selected from the group consisting of 4-(4'-methylbenzyl)imidazole and its non-toxic pharmaceutically acceptable acid addition salts.

34. A compound of claim 1 which is selected from the group consisting of 4-(2'-methoxybenzyl)imidazole and its non-toxic pharmaceutically acceptable acid addition salts.

35. A compound of claim 1 which is selected from the group consisting of 4-(3'-methoxybenzyl)imidazole and its non-toxic pharmaceutically acceptable acid addition salts.

36. A compound of claim 1 which is selected from the group consisting of 4-(4'-methoxybenzyl)imidazole and its non-toxic pharmaceutically acceptable acid addition salts.

37. A compound of claim 1 which is selected from the group consisting of 4-(2'-ethylbenzyl)imidazole and its non-toxic pharmaceutically acceptable acid addition salts.

38. A compound of claim 1 which is selected from the group consisting of 4-(4'-ethylbenzyl)imidazole and its non-toxic pharmaceutically acceptable acid addition salts.

39. A compound of claim 1 which is selected from the group consisting of 4-(2'-chlorobenzyl)imidazole and its non-toxic pharmaceutically acceptable acid addition salts.

40. A compound of claim 1 which is selected from the group consisting of 4-(4'-chlorobenzyl)imidazole and its non-toxic pharmaceutically acceptable acid addition salts.

41. A compound of claim 1 which is selected from the group consisting of 4-(2',6'-dibromobenzyl)imidazole and its non-toxic pharmaceutically acceptable acid addition salts.

42. A compound of claim 1 which is selected from the group consisting of 4-(2'-bromobenzyl)imidazole and its non-toxic pharmaceutically acceptable acid addition salts.

43. A compound of claim 1 which is selected from the group consisting of 4-(2'-fluorobenzyl)imidazole and its non-toxic pharmaceutically acceptable acid addition salts.

44. A compound of claim 1 which is selected from the group consisting of 4-(2',6'-dichlorobenzyl)imidazole and its non-toxic pharmaceutically acceptable acid addition salts.

45. A compound of claim 1 which is selected from the group consisting of 4-(2',6'-difluorobenzyl)imidazole and its non-toxic pharmaceutically acceptable acid addition salts.

46. A compound of claim 1 which is selected from the group consisting of 4-(2',6'-dimethylbenzyl)imidazole and its non-toxic pharmaceutically acceptable acid addition salts.

47. A compound of claim 1 which is selected from the group consisting of 4-(2',3'-dimethylbenzyl)imidazole and its non-toxic pharmaceutically acceptable acid addition salts.

48. A compound of claim 1 which is selected from the group consisting of 4-(2',4'-dimethylbenzyl)imidazole and its non-toxic pharmaceutically acceptable acid addition salts.

49. A compound of claim 1 which is selected from the group consisting of 4-(3',4'-dimethylbenzyl)imidazole and its non-toxic pharmaceutically acceptable acid addition salts.

50. A compound of claim 1 which is selected from the group consisting of 4-(3',5'-dimethylbenzyl)imidazole and its non-toxic pharmaceutically acceptable acid addition salts.

51. A compound of claim 1 which is selected from the group consisting of 4-(2',6'-diethylbenzyl)imidazole and its non-toxic pharmaceutically acceptable acid addition salts.

52. A compound of claim 1 which is selected from the group consisting of 4-(2',4',6'-trimethylbenzyl)imidazole and its non-toxic pharmaceutically acceptable acid addition salts.

53. A compound of claim 1 which is selected from the group consisting of 4-(4'-amino-3',5'-dichlorobenzyl)imidazole and its non-toxic pharmaceutically acceptable acid addition salts.

54. A compound of claim 1 which is selected from the group consisting of 4-(3'-amino-2',6'-dimethylbenzyl)imidazole and its non-toxic pharmaceutically acceptable acid addition salts.

55. A compound of claim 1 which is selected from the group consisting of 5-methyl-4-(2'-methylbenzyl)imidazole and its non-toxic pharmaceutically acceptable acid addition salts.

56. A compound of claim 1 which is selected from the group consisting of 5-methyl-4-(2',3'-dimethylbenzyl)imidazole and its non-toxic pharmaceutically acceptable acid addition salts.

57. A compound of claim 1 which is selected from the group consisting of 4-(2',6'-dimethylbenzyl)-5-methylimidazole and its non-toxic pharmaceutically acceptable acid addition salts.

58. A compound of claim 1 which is selected from the group consisting of 4-(4'-amino-3',5'-dimethylbenzyl)-5-methylimidazole and its non-toxic pharmaceutically acceptable acid addition salts.

59. A compound of claim 1 which is selected from the group consisting of 4-(3',5'-dimethyl-4'-hydroxybenzyl)imidazole and its non-toxic pharmaceutically acceptable acid addition salts.

60. A compound of claim 1 which is selected from the group consisting of 5-methyl-4-($\alpha$-phenyl)hydroxymethylimidazole and its non-toxic pharmaceutically acceptable acid addition salts.

61. A compound of claim 1 which is selected from the group consisting of 5-methyl-4-[$\alpha$-(2'-methylphenyl)]hydroxymethylimidazole and its non-toxic pharmaceutically acceptable acid addition salts.

62. A compound of claim 1 which is selected from the group consisting of 5-methyl-4-[$\alpha$-(2',6'-dimethylphenyl)]hydroxymethylimidazole and its non-toxic pharmaceutically acceptable acid addition salts.

63. A compound of claim 1 which is selected from the group consisting of 5-methyl-4-[$\alpha$-(2',3'-dimethylphenyl)]hydroxymethylimidazole and its non-toxic pharmaceutically acceptable acid addition salts.

64. A compound of claim 1 which is selected from the group consisting of 4-($\alpha$-phenyl)hydroxymethylimidazole and its non-toxic pharmaceutically acceptable acid addition salts.

65. A compound of claim 1 which is selected from the group consisting of 4-[$\alpha$-(2'-methylphenyl)]hydroxymethylimidazole and its non-toxic pharmaceutically acceptable acid addition salts.

66. A compound of claim 1 which is selected from the group consisting of 4-[$\alpha$-(3'-methylphenyl)]hydroxymethylimidazole and its non-toxic pharmaceutically acceptable acid addition salts.

67. A compound of claim 1 which is selected from the group consisting of 4-[$\alpha$-(4'-methylphenyl)]hydroxymethylimidazole and its non-toxic pharmaceutically acceptable acid addition salts.

68. A compound of claim 1 which is selected from the group consisting of 4-[$\alpha$-(2'-methoxyphenyl)]hydroxymethylimidazole and its non-toxic pharmaceutically acceptable acid addition salts.

69. A compound of claim 1 which is selected from the group consisting of 4-[$\alpha$-(3'-methoxyphenyl)]hydroxymethylimidazole and its non-toxic pharmaceutically acceptable acid addition salts.

70. A compound of claim 1 which is selected from the group consisting of 4-[$\alpha$-(4'-methoxyphenyl)]hydroxymethylimidazole and its non-toxic pharmaceutically acceptable acid addition salts.

71. A compound of claim 1 which is selected from the group consisting of 4-[$\alpha$-(2'-ethylphenyl)]hydroxymethylimidazole and its non-toxic pharmaceutically acceptable acid addition salts.

72. A compound of claim 1 which is selected from the group consisting of 4-[$\alpha$-(4'-ethylphenyl)]hydroxymethylimidazole and its non-toxic pharmaceutically acceptable acid addition salts.

73. A compound of claim 1 which is selected from the group consisting of 4-[$\alpha$-(2',6'-dimethylphenyl)]hydrox- 74. A compound of claim 1 which is selected from the group consisting of 4-[α-(2′,3′-dimethylphenyl)]hydroxymethylimidazole and its non-toxic pharmaceutically acceptable acid addition salts.

75. A compound of claim 1 which is selected from the group consisting of 4-[α-(2′,4′-dimethylphenyl)]hydroxymethylimidazole and its non-toxic pharmaceutically acceptable acid addition salts.

76. A compound of claim 1 which is selected from the group consisting of 4-[α-(3′,4′-dimethylphenyl)]hydroxymethylimidazole and its non-toxic pharmaceutically acceptable acid addition salts.

77. A compound of claim 1 which is selected from the group consisting of 4-[α-(3′,5′-dimethylphenyl)]hydroxymethylimidazole and its non-toxic pharmaceutically acceptable acid addition salts.

78. A compound of claim 1 which is selected from the group consisting of 4-[α-(2′,6′-diethylphenyl)]hydroxymethylimidazole and its non-toxic pharmaceutically acceptable acid addition salts.

79. A compound of claim 1 which is selected from the group consisting of 4-[α-(3′-amino-2′,6′-dimethylphenyl)]hydroxymethylimidazole and its non-toxic pharmaceutically acceptable acid addition salts.

80. A compound of claim 1 which is selected from the group consisting of 4-[α-(4′-chlorophenyl)]hydroxymethylimidazole and its non-toxic pharmaceutically acceptable acid addition salts.

81. A compound of claim 1 which is selected from the group consisting of 4-[α-(2′,4′,6′-trimethylphenyl)]hydroxymethylimidazole and its non-toxic pharmaceutically acceptable acid addition salts.

82. A compound of claim 1 which is selected from the group consisting of 4-(α-phenyl)ethoxymethylimidazole and its non-toxic pharmaceutically acceptable acid addition salts.

83. A compound of claim 1 which is selected from the group consisting of 4-[α-(2′-methylphenyl)]methoxymethylimidazole and its non-toxic pharmaceutically acceptable acid addition salts.

84. A compound of claim 1 which is selected from the group consisting of 4-[α-(2′-methylphenyl)]ethoxymethylimidazole and its non-toxic pharmaceutically acceptable acid addition salts.

85. A compound of claim 1 which is selected from the group consisting of 4-[α-(3′-methylphenyl)]ethoxymethylimidazole and its non-toxic pharmaceutically acceptable acid addition salts.

86. A compound of claim 1 which is selected from the group consisting of 4-[α(4′-methylphenyl)]ethoxymethylimidazole and its non-toxic pharmaceutically acceptable acid addition salts.

87. A compound of claim 1 which is selected from the group consisting of 4-[α-(2′-methoxyphenyl)]ethoxymethylimidazole and its non-toxic pharmaceutically acceptable acid addition salts.

88. A compound of claim 1 which is selected from the group consisting of 4-[α-(3′-methoxyphenyl)]ethoxymethylimidazole and its non-toxic pharmaceutically acceptable acid addition salts.

89. A compound of claim 1 which is selected from the group consisting of 4-[α-(4′-methoxyphenyl)]ethoxymethylimidazole and its non-toxic pharmaceutically acceptable acid addition salts.

90. A compound of claim 1 which is selected from the group consisting of 4-[α-(2′,4′, 6′-trimethylphenyl)]ethoxymethylimidazole and its non-toxic pharmaceutically acceptable acid addition salts.

91. A compound of claim 1 which is selected from the group consisting of 4-[α-(2′, 6′-dimethylphenyl)]methoxymethylimidazole and its non-toxic pharmaceutically acceptable acid addition salts.

92. A compound of claim 1 which is selected from the group consisting of 4-[α-(2′,6′-dimethylphenyl)]ethoxymethylimidazole and its non-toxic pharmaceutically acceptable acid addition salts.

93. A compound of claim 1 which is selected from the group consisting of 5-methyl-4-(α-phenyl)ethoxymethylimidazole and its non-toxic pharmaceutically acceptable acid addition salts.

94. A compound of claim 1 which is selected from the group consisting of 5-methyl-4-[α-2′,6′-dimethylphenyl)]methoxymethylimidazole and its non-toxic pharmaceutically acceptable acid addition salts.

95. A compound of claim 1 which is selected from the group consisting of 5-methyl-4-[α-(2′,6′-dimethylphenyl)]ethoxymethylimidazole and its non-toxic pharmaceutically acceptable acid addition salts.

96. A compound of claim 1 which is selected from the group consisting of 4-(2′-methylbenzoyl)imidazole and its non-toxic pharmaceutically acceptable acid addition salts.

97. A compound of claim 1 which is selected from the group consisting of 4-(3′-methylbenzoyl)imidazole and its non-toxic pharmaceutically acceptable acid addition salts.

98. A compound of claim 1 which is selected from the group consisting of 4-(4′-methylbenzoyl)imidazole and its non-toxic pharmaceutically acceptable acid addition salts.

99. A compound of claim 1 which is selected from the group consisting of 4-(2′-methoxybenzoyl)imidazole and its non-toxic pharmaceutically acceptable acid addition salts.

100. A compound of claim 1 which is selected from the group consisting of 4-(3′-methoxybenzoyl)imidazole and its non-toxic pharmaceutically acceptable acid addition salts.

101. A compound of claim 1 which is selected from the group consisting of 4-(4′-methoxybenzoyl)imidazole and its non-toxic pharmaceutically acceptable acid addition salts.

102. A compound of claim 1 which is selected from the group consisting of 4-(2′-ethylbenzoyl)imidazole and its non-toxic pharmaceutically acceptable acid addition salts.

103. A compound of claim 1 which is selected from the group consisting of 4-(4′-chlorobenzoyl)imidazole and its non-toxic pharmaceutically acceptable acid addition salts.

104. A compound of claim 1 which is selected from the group consisting of 4-(2′,6′-dimethylbenzoyl)imidazole and its non-toxic pharmaceutically acceptable acid addition salts.

105. A compound of claim 1 which is selected from the group consisting of 4-(2′,3′-dimethylbenzoyl)imidazole and its non-toxic pharmaceutically acceptable acid addition salts.

106. A compound of claim 1 which is selected from the group consisting of 4-(2′,4′-dimethylbenzoyl)imidazole and its non-toxic pharmaceutically acceptable acid addition salts.

107. A compound of claim 1 which is selected from the group consisting of 4-(3′,4′-dimethylbenzoyl- )imidazole and its non-toxic pharmaceutically acceptable acid addition salts.

108. A compound of claim 1 which is selected from the group consisting of 4-(3',5'-dimethylbenzoyl)imidazole and its non-toxic pharmaceutically acceptable acid addition salts.

109. A compound of claim 1 which is selected from the group consisting of 4-(2',4',6'-trimethylbenzoyl)imidazole and its non-toxic pharmaceutically acceptable acid addition salts.

110. A compound of claim 1 which is selected from the group consisting of 5-methyl-4-(2'-methylbenzoyl)imidazole and its non-toxic pharmaceutically acceptable acid addition salts.

111. A compound of claim 1 which is selected from the group consisting of 4-(2',6'-dimethylbenzoyl)-5-methylimidazole and its non-toxic pharmaceutically acceptable acid addition salts.

112. A compound of claim 1 which is selected from the group consisting of 4-(2',6'-dimethyl-3'-nitrobenzoyl)imidazole and its non-toxic pharmaceutically acceptable acid addition salts.

113. A pharmaceutical composition of matter comprising an anti-ulcer, anti-hypertensive, diuretic, sedative, analgesic, anti-inflammatory or tranquilizing effective amount of a compound of the formula

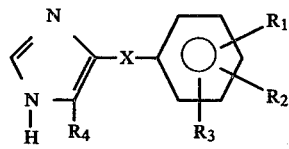

wherein $R_1$, $R_2$ and $R_3$, which can be the same or different, are each hydrogen, chloro, bromo, fluoro, methyl, ethyl, methoxy, amino, hydroxy, or nitro; $R_4$ is hydrogen or alkyl of 1 to 7 carbon atoms; —X— is

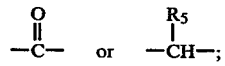

$R_5$ is hydrogen, hydroxy, —$OR_6$—; and $R_6$ is alkyl of 1 to 7 carbon atoms or aryl of 6 to 10 carbon atoms; or a pharmaceutically acceptable acid addition salt or mixture thereof; with the provisos that:
  (a) when $R_1$, $R_2$ and $R_3$ are simultaneously hydrogen, then —X— is other than

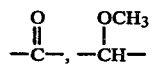

or —$CH_2$—; and
  (b) when $R_1$ is 2-methyl, $R_2$ is 5-methyl, $R_3$ is hydrogen and $R_4$ is methyl, then —X— is other than —$CH_2$—; in combination with a pharmaceutically acceptable inert carrier.

114. A pharmaceutical composition of matter according to claim 113, comprising an anti-ulcer effective amount of a compound of formula (I).

115. A pharmaceutical composition of matter according to claim 114, comprising an anti-ulcer effective amount of 4-(2',6'-dimethylbenzyl)imidazole, 4-(2',3'-dimethylbenzyl)imidazole, 4-(2',4'-dimethylbenzyl)imidazole, 4-(2'-ethylbenzyl)imidazole, 4-(2'-methylbenzyl)imidazole, 4-(3'-methylbenzyl)imidazole, 4-(2',4',6'-trimethylbenzyl)imidazole, 4-(2'-chlorobenzyl)imidazole or 4-(2',6'-dichlorobenzyl)imidazole, as free base, or a non-toxic pharmaceutically acceptable acid addition salt thereof.

116. A pharmaceutical composition of matter according to claim 113, comprising an anti-hypertensive effective amount of 4-(2',6'-dimethylbenzyl)imidazole, 4-(2',3'-dimethylbenzyl)imidazole, 4-(2'-methylbenzyl)imidazole, 4-(2',6'-dichlorobenzyl)imidazole, 4-[α-(2',6'-dimethylphenyl)]hydroxymethylimidazole, 4-[α-(2'-methoxyphenyl)]hydroxymethylimidazole, 4-(2',6'-diethylbenzyl)imidazole, 4-[α-(2',6'-diethylphenyl)]hydroxymethylimidazole or 4-(2',4',6'-trimethylbenzyl)imidazole, as free base, or a non-toxic pharmaceutically acceptable acid addition salt thereof.

117. A pharmaceutical composition of matter according to claim 113, comprising a diuretic effective amount of 4-[α-(2',3'-dimethylphenyl)]hydroxymethylimidazole, 4-[α-(2',6'-dimethylphenyl)]hydroxymethylimidazole, 4-[α-(2'-ethylphenyl)]hydroxymethylimidazole, 4-[α-(2'-methoxyphenyl)]hydroxymethylimidazole, 4-(2',3'-dimethylbenzyl)imidazole, 4-(2',4'-dimethylbenzyl)imidazole, 4-(2',6'-dimethylbenzyl)imidazole, 4-(2'-methylbenzyl)imidazole, 4-[α-(2',6'-dimethylphenyl)]ethoxymethylimidazole, 4-(4'-methylbenzyl)imidazole, 4-(2'-chlorobenzyl)imidazole, 4-(2',4',6'-trimethylbenzyl)imidazole or 4-(3'-methylbenzyl)imidazole, as free base, or a non-toxic pharmaceutically acceptable acid addition salt thereof.

118. A pharmaceutical composition of matter according to claim 113, comprising a sedative effective amount of 4-(2',4'-dimethylbenzyl)imidazole, 4-(2',3'-dimethylbenzyl)imidazole, 4-(3'-methylbenzyl)imidazole, 4-(2',4',6'-trimethylbenzyl)imidazole, 4-(2'-ethylbenzyl)imidazole, 4-(3'-methoxybenzyl)imidazole, 4-(2'-chlorobenzyl)imidazole, 4-[α-(2',3'-dimethylphenyl)]hydroxymethylimidazole, 4-[α-(2'-methoxyphenyl)]hydroxymethylimidazole, or 5-methyl-4-(2',6'-dimethylbenzyl)imidazole, as free base, or a non-toxic pharmaceutically acceptable acid addition salt thereof.

119. A pharmaceutical composition of matter according to claim 113, comprising an analgesic effective amount of 4-(2',6'-dimethylbenzyl)imidazole, 4-(2',3'-dimethylbenzyl)imidazole, 4-(2',4'-dimethylbenzyl)imidazole, 4-(2'-methylbenzyl)imidazole, 4-(3'-methylbenzyl)imidazole, 4-(2'-chlorobenzyl)imidazole, 4-[α-(2',4'-dimethylphenyl)]hydroxymethylimidazole, 4-[α(2',3'-dimethylphenyl)]hydroxymethylimidazole, 4-[α-(2'-methylphenyl)]hydroxymethylimidazole, 4-[α-(3'-methylphenyl)]hydroxymethylimidazole, 4-[α-(4'-methylphenyl)]hydroxymethylimidazole, 4-[α-(2'-ethylphenyl)]hydroxymethylimidazole, 4-[α-(2'-methoxyphenyl)]hydroxymethylimidazole, 4-[α-(3'-methoxyphenyl)]hydroxymethylimidazole, 4-[α(4'-methoxyphenyl)]hydroxymethylimidazole, 4-[α(2',6'-dimethylphenyl)]methoxymethylimidazole, 4-[α-(2',6'-dimethylphenyl)]ethoxymethylimidazole, 5-methyl-4-(2'-methylbenzyl)imidazole, 5-methyl-4-[α-(2',6'-dimethylphenyl)]hydroxymethylimidazole or 4-(2'-ethylbenzyl)imidazole, as free base, or a non-toxic pharmaceutically acceptable acid addition salt thereof.

120. A pharmaceutical composition of matter according to claim 113, comprising an anti-inflammatory effective amount of 4-(2',6'-dimethylbenzyl)imidazole, 4-(2',4'-dimethylbenzyl)imidazole, 4-(3'-methylbenzyl)imidazole, 4-[α-(2',3'-dimethylphenyl)hydroxymethylimidazole, 4-[α-(2'-methylphenyl)]hydroxymethylimidazole, 4-[α-(3'-methylphenyl)]hydroxymethylimidazole, 4-[α-(4'-methylphenyl)]-hydroxymethylimidazole, 4-[α-(2'-ethylphenyl)]hydroxymethylimidazole, 4-[α-(2'-methoxyphenyl)]hydroxymethylimidazole, 4-[α-(3'-methoxyphenyl)]hydroxymethylimidazole, 4-[α-(2',6'-dimethylphenyl)]methoxymethylimidazole, 4-[α-(2',6'-dimethylphenyl)]ethoxymethylimidazole, 4-(4'-methylbenzoyl)imidazole, 5-methyl-4-(2'-methylbenzyl)imidazole, 5-methyl-4-[α-(2',6'-dimethylphenyl)]hydroxymethylimidazole, 5-methyl-4-[α-(2'-methylphenyl)hydroxymethylimidazole or 5-methyl-4-(2'-methylbenzoyl)imidazole, as free base, or a non-toxic pharmaceutically acceptable acid addition salt thereof.

121. A pharmaceutical composition of matter according to claim 113, comprising a tranquilizing effective amount of 4-(2',3'-dimethylbenzyl)imidazole, 4-(2'-chlorobenzyl)imidazole, 4-(2',4',6'-trimethylbenzyl)imidazole, 4-(2',6'-dimethylbenzyl)imidazole, or 4-(3'-methylbenzyl)imidazole, as free base, or a non-toxic pharmaceutically acceptable acid addition salt thereof.

122. A method for treating a mammal exhibiting an ulcerous condition, which comprises administering to said mammal an anti-ulcer effective amount of a compound of the formula:

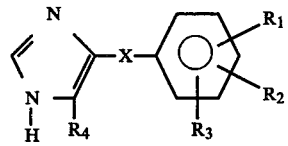

wherein $R_1$, $R_2$ and $R_3$, which can be the same or different, are each hydrogen, chloro, bromo, fluoro, methyl, ethyl, methoxy, amino, hydroxy or nitro; $R_4$ is hydrogen or alkyl of 1 to 7 carbon atoms; —X— is

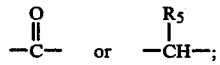

$R_5$ is hydrogen, hydroxy or —$OR_6$; and $R_6$ is alkyl of 1 to 7 carbon atoms or aryl of 6 to 10 carbon atoms; or a non-toxic pharmaceutically acceptable acid addition salt thereof.

123. A method for treating a mammal exhibiting an ulcerous condition, which comprises administering to said mammal an anti-ulcer effective amount of a compound of formula:

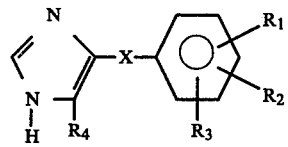

wherein $R_1$, $R_2$ and $R_3$, which can be the same or different, are each hydrogen, chloro, bromo, fluoro, methyl, ethyl, methoxy, amino, hydroxy, or nitro; $R_4$ is hydrogen or alkyl of 1 to 7 carbon atoms; —X— is

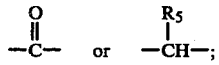

$R_5$ is hydrogen, hydroxy or —$OR_6$; and $R_6$ is alkyl of 1 to 7 carbon atoms or aryl of 6 to 10 carbon atoms; or a pharmaceutically acceptable acid addition salt thereof; with the provisos that:

(a) when $R_1$, $R_2$ and $R_3$ are simultaneously hydrogen, then —X— is other than

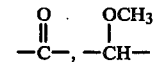

or —$CH_2$—; and (b) when $R_1$ is 2-methyl, $R_2$ is 5-methyl, $R_3$ is hydrogen and $R_4$ is methyl, then —X— is other than —$CH_2$—.

124. A method according to claim 123 wherein the compound of formula (I) is 4-(2',6'-dimethylbenzyl)imidazole, 4-(2',3'-dimethylbenzyl)imidazole, 4-(2',4'-dimethylbenzyl)imidazole, 4-(2'-ethylbenzyl)imidazole, 4-(2'-methylbenzyl)imidazole, 4-(3'-methylbenzyl)imidazole, 4-(2',4',6'-trimethylbenzyl)imidazole, 4-(2'-chlorobenzyl)imidazole or 4-(2',6'-dichlorobenzyl)imidazole, as free base, or a non-toxic pharmaceutically acceptable acid addition salt thereof.

125. A method for treating hypertension in a mammal which comprises administering to said mammal an antihypertensive effective amount of a compound selected from the group consisting of 4-(2',6'-dimethylbenzyl)imidazole, 4-(2',3'-dimethylbenzyl)imidazole, 4-(2'-methylbenzyl)imidazole, 4-(2',6'-dichlorobenzyl)imidazole, 4-[α-(2',6'-dimethylphenyl)]hydroxymethylimidazole, 4-[α-(2'-methoxyphenyl)]hydroxymethylimidazole, 4-(2',6'-diethylbenzyl)imidazole, 4-[α-(2',6'-diethylphenyl)]hydroxymethylimidazole and 4-(2',4',6'-trimethylbenzyl)imidazole, as free bases, and the non-toxic pharmaceutically acceptable acid addition salt thereof.

126. A method for inducing diuresis in a mammal which comprises administering to said mammal a diuretic effective amount of a compound selected from the group consisting of 4-[α-(2',3'-dimethylphenyl)]hydroxymethylimidazole, 4-[α-(2',6'-dimethylphenyl)]hydroxymethylimidazole, 4-[α-(2'-ethylphenyl)]hydroxymethylimidazole, 4-[α-(2'-methoxyphenyl)]hydroxymethylimidazole, 4-(2',3'-dimethylbenzyl)imidazole, 4-(2',4'-dimethylbenzyl)imidazole, 4-(2',6'-dimethylbenzyl)imidazole, 4-(2'-methylbenzyl)imidazole, 4-[α-(2',6'-dimethylphenyl)]ethoxymethylimidazole, 4-(4'-methylbenzyl)imidazole, 4-(2'-chlorobenzyl)imidazole, 4-(2',4',6'-trimethylbenzyl)imidazole and 4-(3'-methylbenzyl)imidazole, as free bases, and the non-toxic pharmaceutically acceptable acid addition salts thereof.

127. A method for inducing sedation in a mammal, which comprises administering to said mammal a sedative effective amount of a compound selected from the group consisting of 4-(2',4'-dimethylbenzyl)imidazole, 4-(2',3'-dimethylbenzyl)imidazole, 4-(3'-methylbenzyl)imidazole, 4-(2',4',6'-trimethylbenzyl)imidazole, 4-(2'-ethylbenzyl)imidazole, 4-(3'-methoxybenzyl)imidazole, 4-(2'-chlorobenzyl)imidazole, 4-[α-(2',3'-dimethylphenyl)]hydroxymethylimidazole, 4-[α-(2'-methoxyphenyl)]hydroxymethylimidazole, and 5-methyl-4-(2',6'-dimethylbenzyl)imidazole, as free bases, and the non-toxic pharmaceutically acceptable acid addition salts thereof.

128. A method for inducing an analgesic response in a mammal, which comprises administering to said mammal an analgesic effective amount of a compound selected from the group consisting of 4-(2',6'-dimethylbenzyl)imidazole, 4-(2',3'-dimethylbenzyl)imidazole, 4-(2',4'-dimethylbenzyl)imidazole, 4-(2'-methylbenzyl)imidazole, 4-(3'-methylbenzyl)imidazole, 4-(2'-chlorobenzyl)imidazole, 4-[α-(2',4'-dimethylphenyl)]hydroxymethylimidazole, 4-[α-(2',3'-dimethylphenyl)]hydroxymethylimidazole, 4-[α-(2'-methylphenyl)]hydroxymethylimidazole, 4-[α-(3'-methylphenyl)]hydroxymethylimidazole, 4-[α-(4'-methylphenyl)]hydroxymethylimidazole, 4-[α-(2'-ethylphenyl)]hydroxymethylimidazole, 4-[α-(2'-methoxyphenyl)]hydroxymethylimidazole, 4-[α-(3'-methoxyphenyl)]hydroxymethylimidazole, 4-[α-(4'-methoxyphenyl)]hydroxymethylimidazole, 4-[α-(2',6'-dimethylphenyl)]methoxymethylimidazole, 4-[α-(2',6'-dimethylphenyl)]ethoxymethylimidazole, 5-methyl-4-(2'-methylbenzyl)imidazole, 5-methyl-4-[α-(2',6'-dimethylphenyl)]hydroxymethylimidazole and 4-(2'-ethylbenzyl)imidazole, as free bases, and the non-toxic pharmaceutically acceptable acid addition salts thereof.

129. A method for treating inflammation in a mammal, which comprises administering to said mammal an anti-inflammatory effective amount of a compound selected from the group consisting of 4-(2',6'-dimethylbenzyl)imidazole, 4-(2',4'-dimethylbenzyl)imidazole, 4-(3'-methylbenzyl)imidazole, 4-[α-(2',3'-dimethylphenyl)]hydroxymethylimidazole, 4-[α-(2'-methylphenyl)]hydroxymethylimidazole, 4-[α-(3'-methylphenyl)]hydroxymethylimidazole, 4-[α-(4'-methylphenyl)]hydroxymethylimidazole, 4-[α-(2'-ethylphenyl)]hydroxymethylimidazole, 4-[α-(2'-methoxyphenyl)]hydroxymethylimidazole, 4-[α-(3'-methoxyphenyl)]hydroxymethylimidazole, 4-[α-(2',6'-dimethylphenyl)]methoxymethylimidazole, 4-[α-(2',6'-dimethylphenyl)]ethoxymethylimidazole, 4-(4'-methylbenzoyl)imidazole, 5-methyl-4-(2'-methylbenzyl)imidazole, 5-methyl-4-[α-(2',6'-dimethylphenyl)]hydroxymethylimidazole, 5-methyl-4-[α-(2'-methylphenyl)]hydroxymethylimidazole and 5-methyl-4-(2'-methylbenzoyl)imidazole, as free bases, and the non-toxic pharmaceutically acceptable acid addition salts thereof.

130. A method for inducing a tranquilizing effect in a mammal, which comprises administering to said mammal a tranquilizing effective amount of a compound selected from the group consisting of 4-(2',3'-dimethylbenzyl)imidazole, 4-(2'-chlorobenzyl)imidazole, 4-(2',4',6'-trimethylbenzyl)imidazole, 4-(2',6'-dimethylbenzyl)imidazole, and 4-(3'-methylbenzyl)imidazole, as free bases, and the non-toxic pharmaceutically acceptable acid addition salts thereof.

131. A process for the preparation of a compound of the formula

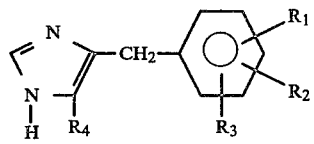

wherein $R_1$, $R_2$ and $R_3$, which can be the same or different, are each hydrogen, chloro, bromo, fluoro, methyl, ethyl, methoxy, amino, hydroxy or nitro; and $R_4$ is hydrogen or alkyl of 1 to 7 carbon atoms; with the provisos that:
(a) $R_1$, $R_2$ and $R_3$ are not simultaneously hydrogen; and
(b) when $R_1$ is 2-methyl, $R_2$ is 5-methyl and $R_3$ is hydrogen, then $R_4$ is other than methyl; which comprises reacting formamide with a compound of the formula

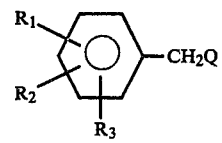

wherein $R_1$, $R_2$ and $R_3$ are defined as above and Q is a radical selected from the group consisting of

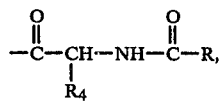

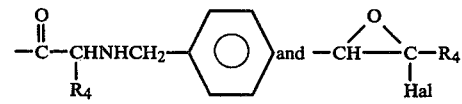

wherein $R_4$ is defined as above, Hal is halogen atom, and R is a substituted or unsubstituted alkyl, aralkyl or aryl group, provided that:
(a) when Q is

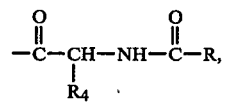

the reaction with formamide is followed by treatment of the intermediate product with acid; and
(b) when Q is

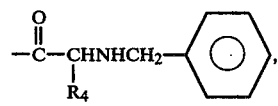

the reaction with formamide is followed by hydrogenation of the intermediate product.

132. A process for the preparation of a compound of the formula

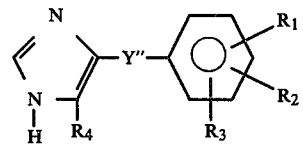

wherein —Y"— is

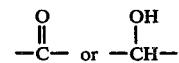

and $R_1$, $R_2$, $R_3$ and $R_4$ are as defined in claim 1, with the proviso that when $R_1$, $R_2$ and $R_3$ are simultaneously hydrogen, then —Y"— is other than

which comprises reacting an imidazole of the formula:

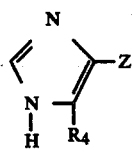

wherein $R_4$ is as defined in claim 1 and Z is —CHO or —COOR wherein —COOR is an ester grouping, with a phenylmagnesiumhalide of the formula:

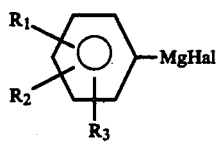

wherein $R_1$, $R_2$ and $R_3$ are as defined above.

133. A process for the preparation of a compound of the formula:

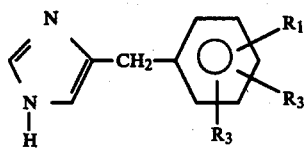

wherein $R_1$, $R_2$ and $R_3$, which can be the same or different, are each selected from the group consisting of hydrogen, chloro, bromo, fluoro, methyl, ethyl, methoxy, amino, hydroxy and nitro, which comprises reacting a starting material of the formula:

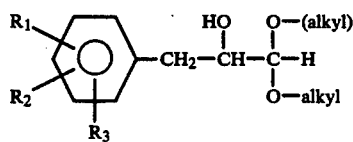

wherein the alkyl groups each have 1 to 7 carbon atoms and $R_1$, $R_2$ and $R_3$ are defined as above, with formamide.

134. A process for the preparation of a compound of the formula

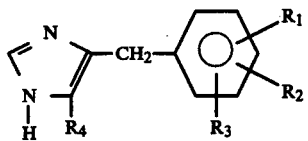

wherein $R_1$, $R_2$ and $R_3$, which can be the same or different, are each hydrogen, chloro, bromo, fluoro, methyl, ethyl, methoxy, amino, hydroxy or nitro; and $R_4$ is hydrogen or alkyl of 1 to 7 carbon atoms; with the provisos that:

(a) $R_1$, $R_2$ and $R_3$ are not simultaneously hydrogen; and
(b) when $R_1$ is 2-methyl, $R_2$ is 5-methyl and $R_3$ is hydrogen, then $R_4$ is other than methyl; which comprises hydrolysis of the corresponding compound of the formula

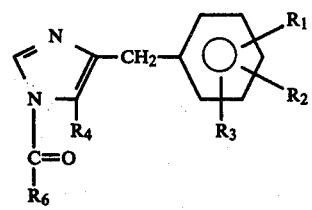

wherein $R_1$, $R_2$, $R_3$ and $R_4$ are defined as above and $R_6$ is alkyl of 1 to 7 carbon atoms or aryl of 6 to 10 carbon atoms, in an aqueous solution of an inorganic acid at elevated temperature.

135. A process for the preparation of a compound of the formula

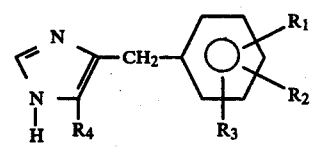

wherein $R_1$, $R_2$ and $R_3$, which can be the same or different, are each hydrogen, chloro, bromo, fluoro, methyl, ethyl, methoxy, amino, hydroxy or nitro; and $R_4$ is hydrogen or alkyl of 1 to 7 carbon atoms; with provisos that:

(a) $R_1$, $R_2$ and $R_3$ are not simultaneously hydrogen; and
(b) when $R_1$ is 2-methyl, $R_2$ is 5-methyl and $R_3$ is hydrogen, then $R_4$ is other than methyl; which comprises hydrogenation of the corresponding compound selected from the group consisting of

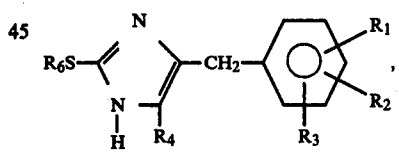

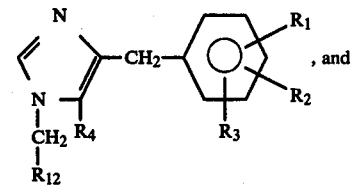

, and

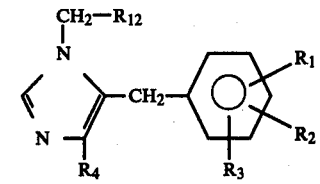

wherein $R_1$, $R_2$, $R_3$ and $R_4$ are defined as above, $R_6$ is alkyl of 1 to 7 carbon atoms or aryl of 6 to 10 carbon atoms and $R_{12}$ is an aryl group, in the presence of a hydrogenation catalyst selected from the group consisting of platinum oxide, palladium-on-carbon and Raney nickel.

136. A process for the preparation of a compound of the formula

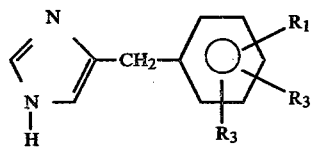

wherein $R_1$, $R_2$ and $R_3$, which can be the same or different, are each hydrogen, chloro, bromo, fluoro, methyl, ethyl, methoxy, amino, hydroxy or nitro; with the proviso that $R_1$, $R_2$ and $R_3$ are not simultaneously hydrogen, which comprises reacting the corresponding compound of the formula

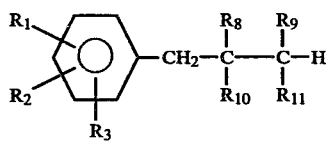
(III)

wherein $R_1$, $R_2$ and $R_3$ are defined as above; $R_8$, $R_9$, $R_{10}$ and $R_{11}$, which can be the same or different, are each hydrogen, hydroxy, halogen, amino, —O—alkyl of 1 to 7 carbon atoms, or

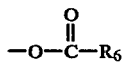

wherein $R_6$ is alkyl of 1 to 7 carbon atoms or aryl of 6 to 10 carbon atoms; or wherein $R_8$ and $R_{10}$ can be combined to form a keto group, or $R_9$ and $R_{11}$ can be combined to form a keto group, or both $R_8$ and $R_{10}$ and $R_9$ and $R_{11}$ can simultaneously form keto groups; with a reagent selected from the group consisting of HN=CH—NH$_2$;

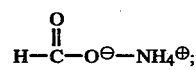

formamide; and a source of ammonia and formaldehyde.

137. The process of claim 136 wherein the reagent is formamide.

138. The process of claim 136 wherein the reagent is a source of ammonia and formaldehyde.

139. The process of claim 138 wherein the reagent is ammonia and formaldehyde.

140. The process of claim 138 wherein the reagent is ammonium acetate and hexamethylenetetramine and wherein, in the compound of formula (I), $R_8$ and $R_9$ form a keto group and $R_9$ and $R_{11}$ form a keto group.

141. A process for the preparation of a compound of the formula

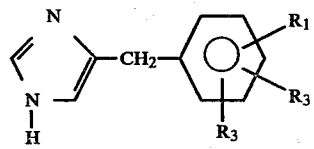

wherein $R_1$, $R_2$ and $R_3$, which can be the same or different, are each hydrogen, chloro, bromo, fluoro, methyl, ethyl, methoxy, amino, hydroxy or nitro; with the proviso that $R_1$, $R_2$ and $R_3$ are not simultaneously hydrogen; which comprises reacting formamide with the corresponding oxazole of the formula

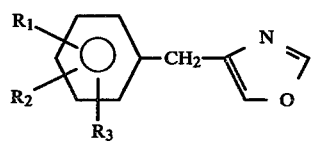

or

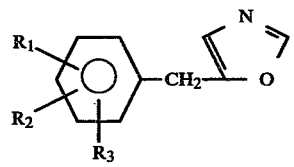

wherein $R_1$, $R_2$ and $R_3$ are defined as above.

* * * * *

UNITED STATES PATENT AND TRADEMARK OFFICE

CERTIFICATE EXTENDING PATENT TERM
UNDER 35 U.S.C. 156

Patent No.    : 4,443,466

Dated         : April 17, 1984

Inventor(s)   : Arto J. Karjalainen et al

Patent Owner  : Farmos-Yhtyma Oy (Farmos Group Ltd)

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

954 DAYS with all rights pertaining thereto as provided by 35 USC 156 (b).

I have caused the seal of the Patent and Trademark Office to be affixed this 7th day of December 1990.

Harry F. Manbeck, Jr.
Assistant Secretary and Commissioner of Patents and Trademarks